United States Patent [19]

Heusler et al.

[11] 4,161,476
[45] Jul. 17, 1979

[54] α-HALO-2-OXO-1-AZETIDINEMETHANE-CARBOXYLIC ACID COMPOUNDS

[75] Inventors: Karl Heusler, Basel, Switzerland; Robert B. Woodward, Cambridge, Mass.

[73] Assignee: Ciba-Geigy Corporation, Ardsley, N.Y.

[21] Appl. No.: 814,763

[22] Filed: Jul. 11, 1977

Related U.S. Application Data

[60] Division of Ser. No. 524,699, Nov. 18, 1974, Pat. No. 4,052,408, which is a continuation of Ser. No. 843,754, Jul. 22, 1969, abandoned.

[30] Foreign Application Priority Data

Jul. 23, 1968 [CH] Switzerland ............... 10994/68
Dec. 11, 1968 [CH] Switzerland ............... 18502/68

[51] Int. Cl.² ................................. C07D 277/62
[52] U.S. Cl. ..................... 260/306.7 C; 424/246; 260/239 A
[58] Field of Search ........................... 260/306.7 C

[56] References Cited

U.S. PATENT DOCUMENTS

| | | | |
|---|---|---|---|
| 3,483,215 | 12/1969 | Woodward | 260/306.7 C |
| 3,755,342 | 8/1973 | Heusler et al. | 260/306.7 C |
| 3,927,013 | 12/1975 | Barton et al. | 260/306.7 C |
| 4,052,408 | 10/1977 | Heusler et al. | 260/306.7 C |

Primary Examiner—Nicholas S. Rizzo
Attorney, Agent, or Firm—John J. Maitner

[57] ABSTRACT

α-Hydroxy-2-oxo-1-azetidinemethane-carboxylic acid compounds of formula

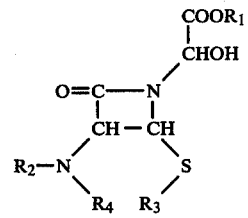

wherein $R_1$ represents a hydrogen atom or the organic residue of an alcohol, $R_2$ represents a hydrogen atom or an acyl residue, $R_3$ represents an organic residue and $R_4$ represents a hydrogen atom, when $R_2$ stands for an acyl residue, or the two groups $R_3$ and $R_4$ together represent a disubstituted carbon atom, when $R_2$ stands for a hydrogen atom or an acyl group, are useful as intermediates for the manufacture of pharmacologically active compounds.

5 Claims, No Drawings

α-HALO-2-OXO-1-AZETIDINEMETHANE-CARBOXYLIC ACID COMPOUNDS

This is a divisional of application Ser. No. 524,699 filed Nov. 18, 1974, now U.S. Pat. No. 4,052,408, which in turn is a continuation of application Ser. No. 843,754, filed July 22, 1969, now abandoned.

SUMMARY OF THE INVENTION

The subject of the present invention are α-hydroxy-2-oxo-azetidinemethane-carboxylic acid compounds of formula

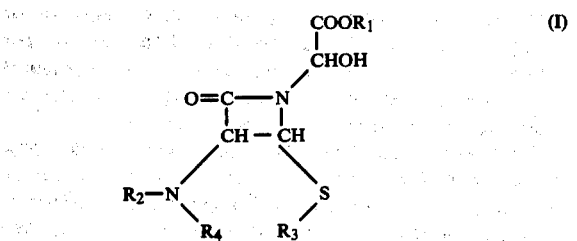

wherein $R_1$ represents a hydrogen atom or the organic residue of an alcohol, $R_2$ represents a hydrogen atom or an acyl residue, $R_3$ represents an organic residue and $R_4$ represents a hydrogen atom, when $R_2$ stands for an acyl residue, or the two groups $R_3$ and $R_4$ together represent a disubstituted carbon atom, when $R_2$ stands for a hydrogen atom or an acyl group, as well as salts of such compounds having salt-forming groupings. These compounds are useful as intermediates, particularly for the manufacture of compounds with anti-bacterial properties.

DESCRIPTION OF THE PREFERRED EMBODIMENTS

The group $R_1$ can denote the organic residue of any alcohol, but especially an optionally substituted aliphatic or araliphatic hydrocarbon residue.

An acyl group $R_2$ primarily represents the acyl residue of an organic carboxylic acid, especially of a carbonic acid semi-derivative or of an optionally substituted aliphatic, cycloaliphatic, cycloaliphatic-aliphatic, aromatic, araliphatic, heterocyclic or heterocyclic-aliphatic carboxylic acid.

An organic residue $R_3$ is an optionally substituted hydrocarbon residue, primarily an aliphatic hydrocarbon residue which can be split off and is preferably unsaturated, or substituted by a hetero-residue, in the linkage position, as well as an appropriate cycloaliphatic, cycloaliphatic-aliphatic or araliphatic hydrocarbon residue which is preferably unsaturated or substituted by a hetero-residue in the linkage position.

Substitutents of a disubstituted carbon atom which is represented by the two residues $R_3$ and $R_4$ together are optionally substituted hydrocarbon residues, such as optionally substituted aliphatic, cycloaliphatic, cycloaliphatic-aliphatic, aromatic or araliphatic hydrocarbon residues. The two substituents of the disubstituted carbon atom can also be taken together and can, for example, represent a bivalent aliphatic hydrocarbon residue which is optionally substituted and/or interrupted by hetero atoms.

An aliphatic hydrocarbon residue is an alkyl, alkenyl or alkynyl residue, especially a lower alkyl or lower alkenyl as well as a lower alkynyl residue, which can, for example, contain up to 7, preferably up to 4, carbon atoms. Such residues can optionally be monosubstituted, disubstituted or polysubstituted by functional groups, for example, by etherified or esterified hydroxyl or mercapto groups, such as lower alkoxy, lower alkenyloxy, lower alkylenedioxy, optionally substituted phenyloxy or phenyl-lower alkoxy, lower alkylmercapto or optionally substituted phenylmercapto or phenyl-lower alkylmercapto, lower alkoxycarbonyloxy or lower alkanoyloxy groups, as well as by halogen atoms, and, furthermore, by acyl residues of organic carboxylic acids, nitro groups, optionally substituted amino groups and/or optionally functionally modified carboxyl groups, such as carbo-lower alkoxy, optionally N-substituted carbamoyl or cyano groups.

Cycloaliphatic or cycloaliphatic-aliphatic hydrocarbon residues are, for example, monocyclic, bicyclic or polycyclic cycloalkyl or cycloalkenyl groups and cycloalkyl- or cycloalkenyl-lower alkyl or -lower alkenyl groups, respectively, wherein cycloalkyl residues, for example, contain up to 12, such as 3-8, preferably 3-6, ring carbon atoms, while cycloalkenyl residues, for example, contain up to 12, for example, 3-8, especially 5-8, preferably 5 or 6 ring carbon atoms, as well as 1 to 2 double bonds, and the aliphatic portion of a cycloaliphatic-aliphatic residue can, for example, contain up to 7, preferably up to 4 carbon atoms. The above cycloaliphatic or cycloaliphatic-aliphatic residues can, if desired, be monosubstituted, disubstituted or polysubstituted, for example, by optionallty substituted aliphatic hydrocarbon residues, such as, for example, the optionally substituted lower alkyl groups mentioned above, or by functional groups, e.g., like the above-mentioned aliphatic hydrocarbon residues.

An aromatic hydrocarbon residue is, for example, a monocyclic or bicyclic aromatic hydrocarbon residue, especially a phenyl residue, as well as a biphenylyl or naphthyl residue, which can optionally be monosubstituted, disubstituted or polysubstituted, for example, like the above-mentioned aliphatic and cycloaliphatic hydrocarbon residues.

An araliphatic hydrocarbon residue is an aliphatic hydrocarbon residue, which is optionally substituted and which, for example, possesses up to three optionallty substituted monocyclic or bicyclic aromatic hydrocarbon residues, and primarily represents a phenyl-lower alkyl or phenyl-lower alkenyl, as well as phenyl-lower alkinyl residue, which residues contain 1-3 phenyl groups and can optionally be monosubstituted, disubstituted or polysubstituted in the aromatic and/or aliphatic portion, for example, like the above-mentioned aliphatic and cycloaliphatic residues.

A bivalent aliphatic hydrocarbon residue is primarily a lower alkylene, as well as a lower alkenylene residue which, for example, contains up to 8, preferably 4 to 5, carbon atoms and which can be substituted, if desired, for example, like the above mentioned cycloaliphatic residues.

The heterocyclic portion of a heterocyclic or heterocyclic-aliphatic residue is especially a monocyclic, as well as bicyclic or polycyclic, azacyclic, thiacyclic, oxacyclic, thiazacyclic, oxazacyclic or diazacyclic residue of aromatic character which can optionally be monosubstituted, disubstituted or polysubstituted, for example, like the above-mentioned cycloaliphatic residues. The aliphatic portion in heterocyclic-aliphatic residues may, for example, possess the substituents listed for the corresponding cycloaliphatic-aliphatic or araliphatic residues.

The acyl residue of a carbonic acid semi-derivative is preferably the acyl residue of a corresponding half-ester, wherein the esterifying organic residue represents an optionally substituted aliphatic, cycloaliphatic, aromatic or araliphatic hydrocarbon residue or a heterocyclic-aliphatic residue, primarily the residue of an optionally substituted lower alkyl half-ester of carbonic acid (i.e. a carbo-lower alkoxy residue which is optionally substituted in the lower alkyl portion), as well as a lower alkenyl, cycloalkyl, phenyl or phenyl-lower alkyl half-ester of carbonic acid, which may optionally be substituted in the lower alkenyl, cycloalkyl, phenyl and phenyl-lower alkyl portion, respectively (i.e. a carbon-lower alkenyloxy, carbo-cycloalkoxy, carbo-phenyloxy or carbo-phenyl-lower alkoxy residue which is optionally substituted in the lower alkenyl, cycloalkyl, phenyl and phenyl-lower alkyl portion, respectively). Acyl residues of a carbonic acid half-ester are furthermore acyl residues of lower alkyl half-esters of carbonic acid, in which the lower alkyl portion contains a heterocyclic group, for example, one of the above-mentioned heterocyclic groups of aromatic character, the lower alkyl residue and the heterocyclic group being optionally substituted. Such acyl residues are carbo-lower alkoxy groups containing in the lower alkyl residue a heterocyclic group of aromatic character and being optionally substituted in the lower alkyl portion and in the heterocyclic group; heterocyclic groups of this nature are described in more detail below.

The acyl residue of an aliphatic carboxylic acid is, for example, the corresponding residue of an alkanecarboxylic, as well as alkenecarboxylic or alkynecarboxylic acid, primarily lower alkanecarboxylic, as well as lower alkenecarboxylic or lower alkynecarboxylic acid, which is optionally substituted, for example, like the above-mentioned aliphatic hydrocarbon residues and which can, for example, contain up to 7, especially up to 4, carbon atoms.

The acyl residue of a cycloaliphatic or cycloaliphatic-aliphatic carboxylic acid is, for example, the acyl residue of a cycloalkane- or cycloalkenecarboxylic acid and cycloalkyl- or cycloalkenyl-lower alkane- or -lower alkenecarboxylic acid, respectively, which is optionally substituted, for example, like the above-mentioned cycloaliphatic or cycloaliphatic-aliphatic hydrocarbon residues, a cyclolkyl or cycloalkenyl residue as well as the aliphatic portion of a cycloaliphatic-aliphatic carboxylic acid having, for example the number of carbon atoms and/or double bonds specified above for corresponding residues and being optionally substituted, for example, as indicated.

The acyl residue of an aromatic carboxylic acid is primarily the residue of a monocyclic or bicyclic aromatic carboxylic acid which can optionally be substituted, for example, like the above-mentioned cycloaliphatic residue.

In the acyl residue of an araliphatic carboxylic acid the araliphatic portion, for example, has the above-mentioned significance; an araliphatic carboxylic acid primarily denotes a phenyl-lower alkanecarboxylic or phenyl-lower alkenecarboxylic acid, wherein the phenyl residue and the aliphatic portion can optionally be substituted, for example, like the above-mentioned cyckloaliphatic or aliphatic groups.

The acyl residue of a heterocyclic carboxylic acid contains especially a heterocyclic residue of aromatic characteristics, which can be monocyclic or bicyclic and primarily represents a corresponding monocyclic or bicyclic, monoazacyclic, monooxacyclic, monothiacyclic, diazacyclic, oxazacyclic or thiazacyclic residue which is optionally substituted, for example, like the above-mentioned cycloaliphatic residue. In the residue of a heterocyclic-aliphatic carboxylic acid, the heterocyclic residue has the significance given above, while the aliphatic portion like, for example, in an araliphatic carboxylic acid, represents an optionally substituted lower alkyl, as well as lower alkenyl residue.

A lower alkyl residue is, for example, a methyl, ethyl, n-propyl, isopropyl, n-butyl, isobutyl, sec.-butyl or tert.-butyl as well as n-phenyl, isopentyl, n-hexyl, isohexyl or n-heptyl group, while a lower alkenyl residue can, for example, be a vinyl, allyl, isopropenyl, 2- or 3-methallyl or 3-butenyl group, and a lower alkynyl residue can, for example, be a propargyl or 2-butynyl group.

Optionally substituted aliphatic hydrocarbon residues, especially lower alkyl groups, which can, inter alia, also be substituents of cycloaliphatic, cycloaliphtic-aliphatic, aromatic, araliphatic, heterocyclic or heterocyclic-aliphatic residues, contain, for example, the above-mentioned substitutents. Such substituted groups are especially halogeno-lower alkyl groups, such as monohalogenated, dihalogenated or polyhalogenated lower alkyl, for example, methyl, ethyl or 1- or 2-propyl groups; residues of this type, especially 2-halogeno-lower alkyl residues, such as 2,2,2-trichloroethyl or 2-iodo-ethyl groups, primarily represent halogenated lower alkyl residues $R_1$.

Other substituted aliphatic hydrocarbon residues, such as aliphatic hydrocarbon residues $R_3$, which are substituted by hetero-residues in the linkage position, are primarily lower alkyl, such as methyl, ethyl, propyl or isopropyl residues containing in the linkage position etherified or esterified hydroxyl groups, for example, lower alkoxy or lower alkanoyloxy groups or halogen atoms. These, as well as aliphatic hydrocarbon residues $R_3$ which are unsaturated in the linkage position, especially the 2-propenyl residue, can preferably be split off under acidic conditions, an alkanoyloxy group also being cleaved off under alkaline conditions, as well as by treatment with heavy metal salts, such as mercury or cadmium salts, capable of forming mercaptides, for example, the corresponding halides or lower alkanoyloxy compounds.

A cycloalkyl group is, for example, a cyclopropyl, cyclobutyl, cyclopentyl, cyclohexyl or cycloheptyl, as well as adamantyl group, and a cycloalkenyl group is, for example, a 2- or 3-cyclopentenyl, 1-, 2- or 3-cyclohexenyl or 3-cycloheptenyl, as well as 2-cyclopropenyl group. A cycloalkyl-lower alkyl or -lower alkenyl residue is, for example, a cyclopropyl-, cyclopentyl-, cyclohexyl- or cycloheptyl-methyl, -1,1-ethyl or -1,2-ethyl, -1,2-ethyl, -1,1-propyl, -1,2-propyl or -1,3-propyl, -vinyl or -allyl group, while a cycloalkenyl-lower alkyl or -lower alkenyl group, for example, represents a 1-, 2- or 3 -cyclopentenyl-, 1-, 2- or 3-cyclohexenyl- or 1-, 2- or 3-cycloheptenyl-methyl, -1,1-ethyl or -1,2-ethyl, -1,1-propyl, -1,2-propyl or -1,3-propyl, -vinyl or -allyl group.

A naphthyl residue is a 1- or 2-naphthyl residue while a biphenylyl group represents, for example, a 4-biphenylyl residue.

A phenyl-lower alkyl or phenyl-lower alkenyl residue, is, for example, a benzyl, 1- or 2-phenylethyl, 1-, 2- or 3-phenylpropyl, diphenylmethyl, trityl, 1- or 2-naphthylmethyl, styryl or cinnamyl residue.

A lower alkylene or lower alkenylene residue is, for example, represented by a 1,2-ethylene, 1,3-propylene, 2,2-dimethyl-1,3-propylene, 1,4-butylene, 1- or 2-methyl-1,4-butylene, 1,4-dimethyl-1,4-butylene, 1,5-pentylene, 1-, 2- or 3-methyl-1,5-pentylene, 1,6-hexylene, 2-buten-1,4-ylene or 2- or 3-penten-1,5-ylene group.

Heterocyclic residues are, for example, monocyclic monoazacyclic, monothiacyclic or monooxacyclic residues of aromatic character, such as pyridyl, for example, 2-pyridyl, 3-pyridyl or 4-pyridyl residues, thienyl, for example, 2-thienyl residues, or furyl, for example, 2-furyl residues, or bicyclic monoazacyclic residues of aromatic character, such as quinolinyl, for example, 2-quinolinyl or 4-quinolinyl residues, or isoquinolinyl, for example 1-isoquinolinyl residues, or monocyclic thiazacyclic or oxazacyclic, as well as diacyclic residues of aromatic character, such as oxazolyl, isoxazolyl, thiazolyl or isothiazolyl, as well as pyrimidinyl residues. Heterocyclic-aliphatic residues are especially lower alkyl or lower alkenyl residues containing heterocyclic residues, such as those mentioned above.

Among the etherified hydroxyl groups there are primarily to be mentioned lower alkoxy groups, for example, methoxy, ethoxy, n-propyloxy, isopropyloxy, n-butyloxy, isobutyloxy, sec.-butyloxy, tert.-butyloxy, n-pentyloxy or tert.-pentyloxy groups, as well as substituted lower alkoxy groups, such as halogeno-lower alkoxy groups, especially 2-halogen-lower alkoxy groups, for example, 2,2,2-trichloroethoxy or 2-iodoethoxy groups, and, furthermore, lower alkenyloxy, for example, vinyloxy or allyloxy groups, lower alkylenedioxy, for example, methylenedioxy or ethylenedioxy, as well as isopropylidenedioxy groups, cycloalkoxy, for example, cyclopentyloxy, cyclohexyloxy or adamantyloxy groups, phenyloxy groups, phenyl-lower alkoxy, for example, benzyloxy or 1- or 2-phenylethoxy groups, or lower alkoxy groups which are substituted by monocyclic monoazacyclic, monooxacyclic or monothiacyclic groups of aromatic character, such as pyridyl-lower alkoxy, for example, 2-pyridylmethoxy, furyl-lower alkoxy, for example, furfuryloxy, or thienyl-lower alkoxy, for example, 2-thenyloxy groups.

By etherified mercapto groups, lower alkylmercapto, for example, methylmercapto or ethylmercapto groups, phenylmercapto groups, or phenyl-lower alkylmercapto, for example, benzylmercapto groups, are to be understood.

Esterified hydroxyl groups are primarily halogen atoms, for example, fluorine, chlorine, bromine or iodine atoms, as well as lower alkanoyloxy groups, for example, acetoxy or propionyloxy groups.

Substituted amino groups are monosubstituted or disubstituted amino groups, in which the substituents primarily present optionally substituted monovalent or divalent aliphatic, cycloaliphatic, cycloaliphatic-aliphatic, aromatic or araliphatic hydrocarbon residues, as well as acyl groups. Such amino groups are especially lower alkylamino or di-lower alkylamino groups, for example, methylamino, ethylamino, dimethylamino or diethylamino groups, or lower alkyleneamino groups, which are optionally interrupted by hetero-atoms, such as oxygen or sulphur atoms, or nitrogen atoms which are optionally substituted, for example, by lower alkyl groups, such as pyrrolidino, piperidino, morpholino, thiamorpholino or 4-methylpiperazino groups, as well as acylamino, particularly lower alkanoylamino, such as acetylamino or propionylamino groups.

A carbo-lower alkoxy residue is, for example, a carbomethoxy, carbethoxy, carbo-n-propyloxy, carbo-isopropyloxy, carbo-tert.-butyloxy or carbo-tert.-pentyloxy group.

Optionally N-substituted carbamoyl groups are, for example, N-lower alkylcarbamoyl or N,N-di-lower alkylcarbamoyl groups, such as N-methyl-, N-ethyl-, N,N-dimethyl or N,N-diethylcarbamoyl groups.

A carbo-lower alkenyloxy residue is, for example, the carbovinyloxy group, while carbo-cycloalkoxy and carbo-phenyl-lower alkoxy groups, in which the cycloalkyl- or phenyl-lower alkyl residue have the above-mentioned significance represent, for example, carbo-adamantyloxy or carbo-benzyloxy, as well as carbo-diphenylmethoxy or carbo-($\alpha$-4-biphenylyl-$\alpha$-methylethoxy) groups. Carbo-lower alkoxy groups, in which the lower alkyl residue contains monocyclic monoazacyclic, monooxacyclic or monothiacyclic groups are, for example, carbo-furyl-lower alkoxy, such as carbofurfuryloxy groups, or carbo-thienyl-lower alkoxy, for example, carbo-2-thenyloxy groups.

A lower alkanecarboxylic or lower alkenecarboxylic acid is, for example, acetic, propionic, butyric, isobutyric, valeric, pivalic or acrylic acid, while a cycloalkanecarboxylic or cycloalkenecarboxylic acid and a cycloalkyl- or cycloalkenyl-lower alkane- or -lower alkenecarboxylic acid, respectively, is, for example, a cyclopentanecarboxylic, cyclohexanecarboxylic or 3-cyclohexenecarboxylic acid, and a cyclopentylpropionic, cyclohexylacetic, 3-cyclohexenylacetic or hexahydrocinnamic acid, respectively.

A monocyclic or bicyclic aromatic carboxylic acid is, for example, benzoic acid or 1- or 2-naphthalenecarboxylic acid, and a phenyl-lower alkanecarboxylic or phenyl-lower alkenecarboxylic acid, for example, a phenylacetic, phenylpropionic or cinnamic acid.

As heterocyclic carboxylic acids, nicotinic acid or isonicotinic acid, 2-thiophenecarboxylic, 2-furanecarboxylic, 2- or 4-quinolinecarboxylic or 1-isoquinolinecarboxylic acid may be mentioned, and as corresponding lower alkanecarboxylic or lower alkenecarboxylic acids substituted by heterocyclic residues, for example, 2-, 3- or 4-pyridylacetic, 2-thienylacetic, 2-furylacetic or 2-furylacrylic acid may be mentioned.

The compounds of the present invention may be in the form of mixtures of isomers or in the form of pure isomers.

The compounds according to the invention represent novel intermediates which are suitable for the manufacture of valuable compounds which primarily exhibit pharmacological properties. Thus, it is, for example, possible, in compounds of formula I, in which $R_1$ denotes an organic, primarily an easily removable organic residue $R_1^a$ of an alcohol, for example, an organic residue of an alcohol which can be removed by reduction, such as a 2-halogeno-lower alkyl, for example, the 2,2,2-trichloroethyl or the 2-iodoethyl residue, or an organic residue of an alcohol which can be removed under acid conditions, such as a methyl residue which is polysubstituted by optionally substituted aliphatic or aromatic hydrocarbon residues, for example, the benzhydryl, trityl, tert.-butyl or tert.-pentyl, as well as the adamantyl residue, $R_2$ represents an acyl residue $R_2^A$ preferably an acyl residue $R_2^a$, which is easily removable, for example, under acid conditions, above all the acyl residue of a half-ester of carbonic acid, for example, the carbo-tert.-butyloxy, carbo-tert.-pentyloxy, carbo-vinyloxy, carbo-adamantyloxy or carbo-furfuryloxy, as well as carbo-diphenylmethoxy or carbo-(α-4-biphenylyl-α-methyl-ethoxy) residue, $R_3$ and $R_4$ have the above-mentioned significance and are primarily taken together and represent a carbon atom which is disubstituted, preferably by lower alkyl, especially methyl groups, to replace the hydroxyl group by a reactive esterfied hydroxyl group, especially a halogen atom, for example, by treatment with suitable halogenating agents, for example, a thionyl halide, such as chloride, or a phosphorus oxyhalide, such as oxychloride, as well as a suitable sulfonic acid halide, such as chloride, preferably in the presence of a base, such as triethylamine, diisopropylethylamine or pyridine. From the resulting compounds of the formula

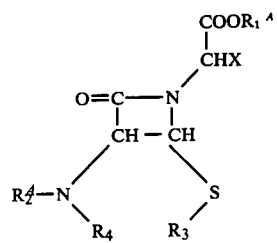 (A)

in which X is a reactive esterified hydroxy group, especially a halogen, primarily a chlorine, as well as a bromine atom, and in which $R_1{}^A$ is one of the above, for example, an easily removable organic residue, by reaction with phosphine compounds of formula $P(R_a)(R_b)(R_c)$, wherein each of the residues $R_a$, $R_b$ and $R_c$ represents an optionally substituted hydrocarbon residue, especially an optionally substituted aliphatic or aromatic hydrocarbon residue, for example, with triphenylphosphine or tributylphosphine, via the corresponding phosphonium salts, preferably by treatment with a basic reagent, one obtains the phosphorane compounds of the formula

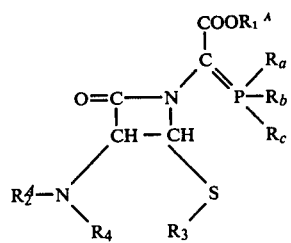 (B)

wherein $R_1{}^A$ and $R_2{}^A$ preferably represent the above-mentioned removable residues $R_1{}^a$ and $R_2{}^a$, respectively. These compounds represent starting substances of the "Wittig"-type which can be used for numerous purposes.

Compounds of the type of formula B can, for example, be reacted with carboxaldehyde compounds of the formula

 (C)

wherein R represents a free or etherified hydroxyl group or a carbon atom which, in addition to at least one hydrogen atom, contains optionallty substituted hydrocarbon residues, especially optionally substituted aromatic, as well as aliphatic hydrocarbon residues, such as phenyl groups, as well as lower alkyl group, or tautomers or reactive derivatives thereof, such as for example, the hydrates or enols thereof, the reaction being preferably carried out at an elevated temperature, for example, at about 50° C. to about 150° C., and in an inert solvent, such as a hydrocarbon, for example, toluene or xylene, or in an ether, for example, dioxane or diethyleneglycol dimethyl ether, or a solvent mixture. Compounds of the formula

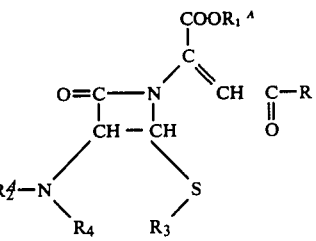

wherein R, $R_1{}^A$, $R_3$ and $R_4$ have the above-mentioned significance, especially the preferred significance, and in which $R_2{}^A$ stands for an easily removable (particularly under acidic conditions) acyl residue $R_2{}^a$, are thus obtained.

In compounds of formula D, in which R represents a free or etherified hydroxyl group, especially a lower alkoxy, for example, amethoxy, ethoxy, tert.-butyloxy or tert.-pentyloxy group, a halogeno-lower alkoxy, for example, 2,2,2-trichloroethoxy group, a cycloalkoxy, for example, adamantyloxy group, a phenyl-lower alkoxy, for example, benzhydryloxy group, or a furyl-lower alkoxy, for example, furfuryloxy group, the double bond can be saturated, for example, by treatment with catalytically activated hydrogen, for example, in the presence of a noble metal catalyst, such as a palladium catalyst, a chemical reducing agent, for example, by treatment with a suitable zinc compound, such as zinc, zinc amalgam or zinc-copper, e.g., in the presence of a reagent capable of furnishing hydrogen, such as a weak carboxylic acid, for example, acetic acid, or a lower alkanol, such as methanol, ethanol or isopropanol, if desired, an aqueous mixture thereof, or a homogenous hydrogenation catalyst, such as a transition metal hydride, for example, a corresponding chromium-III, manganese-II, iron-III, cobalt-II or nickel-II compound or a complex, such as a carbonyl, cyano or phosphine complex thereof. On treatment with a strong, preferably oxygen-containing, inorganic or organic acid, primarily trifluoroacetic acid, in the presence of an anhydride of a strong acid, for example, trifluoracetic acid anhydride, if necessary, followed by an additional acid anhydride, especially acetic acid anhydride, a resulting compound of the formula

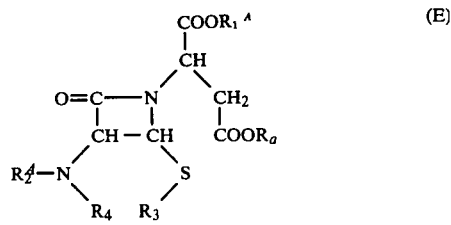 (E)

wherein R$_a$ represents a hydrogen atom or one of the easily removable organic residues of an alcohol R$_1^a$ mentioned for the group R$_1^A$, and in which R$_2^A$ stands for an easily removable (particularly under acidic conditions) acyl residue R$_2^a$, can, optionally after removal of an easily removable acyl group R$_2^A$ and/or conversion of an intermediate of formula E, wherein R$_a$ represents a hydrogen atom into a reactive derivative, such as an acid halide, for example, acid chloride (using, for example, thionyl chloride or oxalyl chloride), or a mixed anhydride, for example, with a carbonic acid lower alkyl half-ester, such as ethyl half-ester (using, for example, a halogenoformic acid lower alkyl ester) or with a lower alkanecarboxylic acid, such as acetic acid (using, for example, a corresponding anhydride), be ring-closed, with splitting of the R$_3$—S—bond, as well as of the R$_4$—N—bond to give a compound of the formula

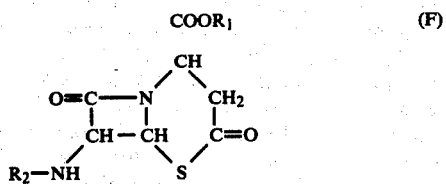 (F)

and, if desired, in a resulting compound a hydrogen atom R$_2$ can optionally be replaced by an acyl group and/or an organic residue R$_1$ can optionally be replaced by hydrogen. Compounds of the type (E), primarily those, in which R$_1$ represents a hydrogen atom and R$_2$ represents an acyl group, are antibiotically active against various micro-organisms, for example, against gram-positive and gram-negative bacteria, such as *Staph. aureus, Proteus vulgaris* and *Bacillus megatherium*, and are useful accordingly.

Furthermore, compounds of the type of formula D, in which R$_1^A$ denotes an organic, especially an easily removable, for example, reductively removable organic residue of an alcohol R$_1^a$, such as a 2-halogen-lower alkyl, for example, the 2,2,2-trichlorethyl residue, or an organic residue of an alcohol which can be removed under acid conditions, such as a methyl residue which is polysubstituted by optionally substituted aliphatic or aromatic hydrocarbon residues, for example, the benzhydryl, trityl, tert.-butyl, tert.-pentyl or adamantyl residue, R$_2^A$ represents an easily, for example, under acidic conditions, removable acyl residue R$_2^a$, such as the acyl residue of a half-ester of carbonic acid, removable, for example, under acid conditions, such as the carbo-tert.-butyloxy, carbo-tert.-pentyloxy, carbovinyloxy, carboadamantyloxy or carbo-furfuryloxy, as well as carbodiphenylmethoxy or carbo-(α-4-biphenylyl-α-methylethoxy) residue, R$_3$ and R$_4$ have the above-mentioned significance and are primarily taken together to represent a carbon atom which is disubstituted, preferably by lower alkyl, especially methyl groups, and R represents a carbon atom which apart from at least one hydrogen atom contains optionally substituted hydrocarbon residues or also optionally substituted heterocyclic or heterocyclic-aliphatic residues, in which heterocyclic groups possess aromatic character, or contains functional groups, and especially represents a corresponding carbon atom which preferably contains as substitutents one or two lower alkyl groups or a phenyl group optionally substituted as mentioned above, for example, by hydrocarbon residues, such as lower alkyl groups or by functional groups, such as the etherified or esterified hydroxyl groups, for example, lower alkoxy groups or halogen atoms, or nitro groups, such a phenyl group optionally also together with a lower alkyl group, or an acyl group, for example, an optionally substituted benzoyl group, can be ring-closed by treatment with a suitable acid reagent, for example, trifluoroacetic acid. In resulting compounds of the formula

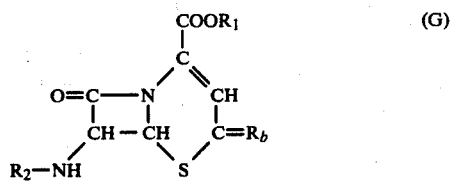 (G)

wherein R$_b$ represents a carbon atom which is substituted by optionally substituted hydrocarbon residues, optionally substituted heterocyclic or heterocyclic-aliphatic residues, wherein heterocyclic groups possess aromatic character, or functional groups, an organic group R$_1$ can be replaced by hydrogen and/or a hydrogen atom R$_1$ and/or R$_2$ can be replaced by an organic group R$_1$ and an acyl residue R$_2$, especially by a suitable acyl residue, respectively.

Compounds of type (G), especially those in which R$_1$ represents a hydrogen atom and R$_2$ represents a suitable acyl residue of an organic carboxylic acid, especially an acyl residue occurring in pharmacologically active 6-acyl-aminopenicillanic acid derivatives or 7-acylaminocephalosporanic acid derivatives, show excellent antibiotic effects against various micro-organisms, especially gram-positive bacteria, such as *Staph. aureus* and *Proteus vulgaris* and can be useful accordingly.

The invention primarily relates to compounds of the formula

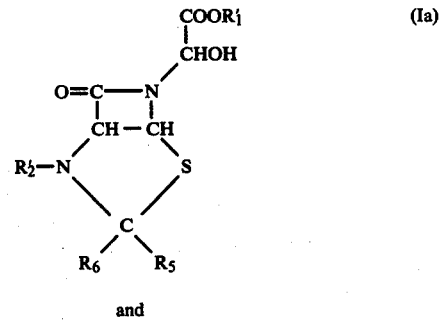 (Ia)

and

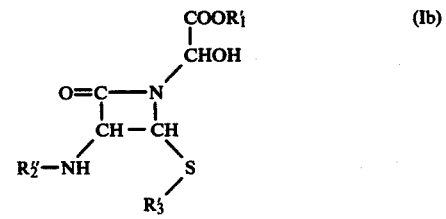 (Ib)

wherein R$_1$' represents a hydrogen atom or a lower alkyl, such as a methyl or ethyl, especially a tert.-butyl, as well as tert.-pentyl residue, a halogeno-lower alkyl, primarily a 2-halogeno-lower alkyl, such as a 2,2,2-trichloroethyl residue, a cycloalkyl, for example, adamantyl residue, or a phenyl-lower alkyl, especially diphenylmethyl residue, particularly an easily removable organic residue of the above type, $R_2'$ represents a hydrogen atom or the residue $R_2''$, $R_2''$ represents an acyl residue, especially an acyl residue occurring in pharmacologically active N-acyl derivatives of 6-aminopenicillanic acid or 7-amino-cephalosporanic acid, such as a phenylacetyl, phenyloxyacetyl, phenylglycyl (optionally having a protected amino group), thienylacetyl, for example, 2-thienylacetyl, chloroethylcarbonyl or cyanoacetyl residue, or an easily removable acyl residue, especially the residue of a half-ester of carbonic acid, such as a carbo-lower alkoxy, for example, carbo-tert.-butyloxy or carbo-tert.-pentyloxy residue, a carbo-cycloalkoxy, for example, carboadamantyloxy residue, or a carbo-furyl-lower alkoxy, for example, carbofurfuryloxy residue, as well as a carbo-diphenylmethoxy or carbo-($\alpha$-4-biphenylyl-$\alpha$-methyl-ethoxy) residue, each of the residues $R_5$ and $R_6$ represents a lower alkyl, especially a methyl residue, and $R_3'$ denotes the 2-propenyl or a 2-lower alkanoyloxy-2-propyl, such as 2-acetoxy-2-propyl group.

Particularly valuable intermediates are the $\alpha$-(2-carbo-lower alkoxy-3,3-dimethyl-7-oxo-4-thia-2,6-diaza-6-bicyclo[3,2,0]heptyl)-$\alpha$-hydroxy-acetic acid lower alkyl esters, wherein the lower alkyl residue of the ester grouping may optionally possess one or more halogen atoms, preferably in 2-position, and primarily represents the tert.-butyl or 2,2,2-trichloroethyl residue, while the carbo-lower alkoxy residue in the 2-position preferably represents the carbo-tert.-butyloxy residue.

The compounds of the present invention can be obtained in a surprising manner, when a 1-unsubstituted azetidin-2-one compound of formula

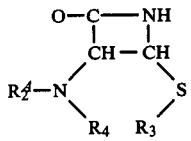 (II)

wherein $R_2^A$ represents an acyl residue, is reacted with a compound of formula

 (III)

wherein $R_1^A$ represents the organic residue of an alcohol, or with a reactive derivative thereof, and, if desired, the acyl group $R_2^A$ is split off in a resulting compound, and, if desired, in a compound thus obtained the free nitrogen atom is acylated, and/or the resulting ester compound is converted to the corresponding free acid compound, and, if desired, a free carboxylic acid compound thus obtained is converted to an ester, and/or, if desired, a resulting compound having a salt-forming group is converted into a salt or a resulting salt into the free compound or into another salt, and/or, if desired, a resulting isomer mixture is resolved into the individual isomers.

The above reaction, that is to say the addition of the glyoxylic acid ester compound to the nitrogen atom of the lactam ring, preferably takes place at an elevated temperature, primarily at about 50° C. to about 150° C. and, in particular, in the absence of a condensing reagent and/or without the formation of a salt, it being also possible to use, instead of the glyoxylic acid compound, a reactive oxo-derivative thereof. The latter is primarily a hydrate, with any resulting water, if necessary, being removed by distillation, for example, azeotropically.

The process is preferably carried out in the presence of a suitable solvent, such as, for example, dioxane or toluene, or solvent mixture, if desired or required, in a closed vessel under pressure and/or in the atmosphere of an inert gas, such as nitrogen.

In a resulting compound an acyl group $R_2^A$, especially an easily removable acyl residue, can be split off in a manner which is in itself known, a carbo-tert.-butyloxy group, for example, by treatment with trifluoroacetic acid, a carbo-2,2,2-trichloroethoxy group, for example, by treatment with a suitable metal or metal compound, for example, zinc or with a chromium-II compound, such as chromium-II chloride or acetate, preferably in the presence of a hydrogen-furnishing compound capable of producing nascent hydrogen together with the metal or metal compound, such as aqueous acetic acid.

In a compound obtained in this way the unsubstituted nitrogen atom in the 3-position can be acylated according to methods which are in themselves known, for example, by treatment with carboxylic or sulphonic acids or acid derivatives thereof, such as halides, for example, chlorides, or anhydrides (whereby there are also to be understood the internal anhydrides of carboxylic acids, i.e. ketenes, or of carbamic or thiocarbamic acids, i.e. isocyanates or isothiocyanates) or activated esters, whereby suitable condensing reagents, such as carbodiimides, for example, dicyclohexylcarbodiimide, may be used, if necessary.

In a resulting compound an ester grouping can be converted to the free carboxyl group; for example, a carbodiphenylmethoxy or carbo-tert.-butyloxy group can be converted by treatment with an acid reagent, such as trifluoroacetic acid. A carboxyl group esterified by a 2-halogeno-lower alkanol, especially 2,2,2-trichloroethanol, as well as 2-iodoethanol, can be converted to the free carboxyl group by treatment with chemical reducing agents, for example, by the action of treatment with reducing metals, metal alloys or metal amalgams, preferably in the presence of hydrogen-furnishing compounds capable of producing nascent hydrogen with the metals, metal alloys or metal amalgams, such as zinc, zinc alloys, for example, zinc-copper, or zinc amalgam, preferably in the presence of acids, which optionally contain water, such as organic carboxylic acids, for example, lower alkanecarboxylic acids, primarily acetic acid, or alcohols, such as lower alkanols, or alkali metal amalgams, e.g. sodium or potassium amalgam, or aluminium amalgam in the presence of a moist solvent, such as ether, and also by treatment with strongly reducing metal salts, such as chromium-II compounds, for example, chromium-II-chloride or chromium-II-acetate, preferably in the presence of an aqueous medium containing organic solvents miscible with water, such as lower alkanols, lower alkanecarboxylic acids or ethers, for example, methanol, ethanol, acetic acid, tetrahydrofuran, dioxane, ethylene glycol dimethyl ether or diethylene glycol dimethyl ether.

A resulting free carboxylic acid compound can be converted into its salts, such as, for example, alkali or alkaline earth metal or ammonium salts, or into its esters in a manner which is in itself known. Free carboxyl groups can, for example be esterified by treatment with a diazo compound, such as a diazo-lower alkane, for example, diazomethane or diazoethane, or a phenyl-diazo-lower alkane, for example, phenyldiazomethane or diphenyldiazomethane, or by reaction with an alcohol suitable for esterification in the presence of an esterifying reagent, such as a carbodiimide, for example, dicyclohexylcarbodiimide, as well as carbonyl-diimideazole, or according to any other known and suitable esterification procedure, such as reaction of a salt of the acid with a reactive ester of an alcohol and of a strong inorganic acid, as well as of a strong organic sulphonic acid. Furthermore, acid halides, such as acid chlorides (manufactured, for example by treatment with oxalyl chloride), or activated esters, for example, esters with N-hydroxy-nitrogen compounds, or mixed anhydrides formed, for example, with halogenoformic acid lower alkyl esters, such as chloroformic acid ethyl esters, can be converted into the esters by reaction with alcohols, optionally in the presence of a base, such as pyridine.

Resulting mixtures of isomers can be resolved into the individual isomers according to methods which are in themselves known, for example, by fractional crystallisation, adsorption chromatography (column or thin layer chromatography) or other suitable resolution processes. Resulting racemates can be resolved into the antipodes in the usual manner, for example, by forming a mixture of diastereoisomeric salts with optically active, salt-forming reagents, resolving the mixture into the diastereoisomeric salts and converting the separated salts into the free compounds, or by fractional crystallization from optically active solvents.

The process also comprises those modifications, according to which compounds resulting as intermediates are used as starting substances and the remaining process stages are carried out with these, or according to which the process is stopped at any stage; furthermore, starting materials can be used in the form of derivatives or formed during the reaction.

Preferably those starting materials are used and those reaction conditions are chosen, which lead to the compounds previously mentioned as being particularly preferred.

Starting materials used in accordance with the process, in which $R_3$ and $R_4$ together represent a disubstituted carbon atom, are known. Others, in which $R_3$ denotes a removable organic residue and $R_4$ stands for a hydrogen atom, can, for example, be obtained, when in a 6-N-acylamino-penicillanic acid compound the carboxyl group is converted into an isocyanato group in a manner which is in itself known, the compound thus obtained is treated with a 2-halogeno-lower alkanol, for example, 2,2,2-trichloroethanol or 2-iodoethanol, and the substituent in the 2-position in a resulting 6-acylamino-2-(N-carbo-2-halogeno-lower alkoxyamino)-3,3-dimethyl-4-thia-1-azabicyclo[3,2,0]heptan-7-one compound is split by treatment with a chemical reducing agent, for example, zinc in the presence of 90% strength acetic acid. The resulting 6-acylamino-2-hydroxy-3,3-dimethyl-4-thia-1-azabicyclo[3,2,0]heptan-7-one compound is treated with a heavy metal acylate oxidising reagent, especially a lead-IV-carboxylate, such as a lead-IV-lower alkanoate, for example, lead tetraacetate, usually with irradiation, preferably with ultra-violet light, can be converted to a 3-acylamino-2-(2-acyloxy-2-propylmercapto)-1-formyl-azetidin-4-one compound. If desired, the acyloxy group together with hydrogen can be split off in the form of the corresponding acid by heating, and with formation of the 2-propenylmercapto grouping. The formyl group attached to the ring nitrogen atom can be removed by treatment with a suitable decarbonylation agent, such as a tris-(tri-organically substituted phosphine)-rhodium halide, for example, tris-(triphenylphosphine)-rhodium chloride, in a suitable solvent, e.g. benzene, as well as by hydrolysis, for example, with an aqueous alkali metal hydroxide, or by ammonolysis with aqueous ammonia in the presence of an organic solvent, which is only slightly miscible with water, or with conversion of the formyl group into the carbinol group, for example, by treatment with catalytically activated hydrogen in the presence of an acid reagent, such as with hydrogen in the presence of a palladium catalyst and glacial acetic acid or tetrahydrofuran containing hydrochloric acid. If desired, the 2-acyloxy-2-propyl residue of a resulting compound can be replaced by another organic residue by treatment with a weakly basic reagent, such as an alkali metal hydrogen carbonate or pyridine, in the presence of a reactive ester of an alcohol, such as a suitable halide.

The present invention also includes the compounds of the formula A (manufactured from those of the formula I), in which $R_1$, $R_2^A$, $R_3$ and $R_4$ have the previously given meaning, and in which a reactive esterified hydroxyl group is primarily a halogen, such as a chlorine or bromine atom, as well as an organic, for example, aliphatic or aromatic, sulfonyloxy group, such as a lower akyl, e.g. methyl- or ethylsulfonyloxy group, or an aryl, e.g. phenyl-, 4-methylphenyl-, 4-bromophenyl- or 3-nitrophenylsulfonyloxy group. These are primarily the compounds of the formulae

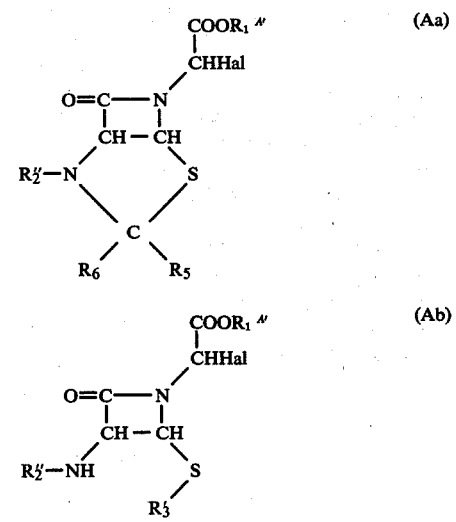

in which $R_1^{A'}$ represents one of the organic residues $R_1'$, $R_2'$, $R_3'$, $R_5$ and $R_6$ have the previously given meaning and Hal stands for a chlorine or bromine atom. Especially mentioned are the α-(2-carbo-lower alkoxy-3,3-dimethyl-7-oxo-4-thia-2,6-diaza-6-bicyclo[3,2,0]heptyl)-α-Hal acetic acid lower alkyl esters, in which Hal has the above given meaning, and the lower alkyl residue of the ester grouping optionally possesses one or more halogen atoms, preferably in the 2-position, and primarily represents the tert.-butyl or 2,2,2-trichloroethyl residue, while the carbo-lower alkoxy residue in the 2-position preferably represents the carbo-tert.-butyloxy residue.

The compounds of the formula A can be obtained, when in an α-hydroxy-2-oxo-1-azetidine-methanecarboxylic acid ester of the formula I, wherein $R_1$ represents the organic residue of an alcohol and $R_2$ represents an acyl group $R_2^A$, the hydroxyl group is converted to a reactive esterified hydroxyl group by treatment with an esterifying acid derivative, and, if desired, in a resulting compound, a reactive esterified hydroxyl group is converted into another reactive esterified hydroxyl group, and/or, if desired, a resulting compound having a salt-forming group is converted to a salt or a resultng salt is converted to the free compound or to another salt and/or, if desired, a resulting isomer mixture is resolved into the individual isomers.

The above reaction is carried out by treating the starting material with a suitable halogenating agent, such as a thionyl halide, for example, thionyl chloride, a phosphorus oxyhalide, especially phosphorus oxychloride, or a halogenophosphonium halide, such as triphenylphosphine dibromide or diiodide, as well as by treatment with a suitable organic sulphonic acid halide, such as chloride, preferably in the presence of a basic reagent, primarily of an organic basic reagent, such as an aliphatic tertiary amine, for example, triethylamine or diisoproylethylamine, or a heterocyclic base of the pyridine type, for example, pyridine or collidine.

The process is preferably carried out in the presence of a suitable solvent, for example, dioxane or tetrahydrofuran, or of a solvent mixture, if necessary, while cooling and/or in the atmosphere of an inert gas, such as nitrogen.

In a resulting compound, a reactive esterified hydroxyl group X can be converted into another reactive hydroxyl group in a manner which is in itself known. Thus, for example, a chlorine atom can be replaced by a bromine or iodine atom by treating the corresponding chlorine compound with a suitable bromine or iodine compound, especially with an inorganic bromide or iodide salt, such as lithium bromide, preferably in the presence of a suitable solvent, such as ether.

Also included within the scope of the present invention are compounds of the formula B, in which $R_1^A$, $R_2^A$, $R_3$ and $R_4$ have the previously given meaning, and each of the groups $R_a$, $R_b$ and $R_c$ represents an optionally substituted hydrocarbon residue, primarily an optionally substituted aliphatic or aromatic, as well as also an optionally substituted cycloaliphatic, cycloaliphatic-aliphatic or araliphatic hydrocarbon residue. These compounds are especially those of the formulae

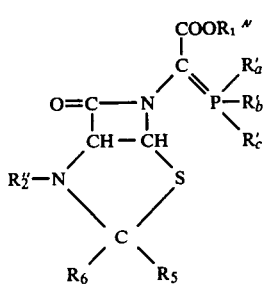

(Ba)

and

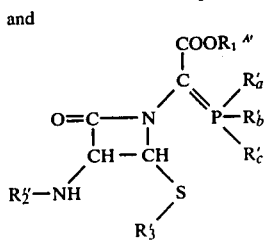

(Bb)

in which $R_1^{A'}$, $R_2''$, $R_3'$, $R_5$ and $R_6$ have the previously given meaning, and each of the groups $R_a'$, $R_b'$ and $R_c'$ represents a lower alkyl residue, which is optionally substituted, for example, by etherified or esterified hydroxyl groups, such as lower alkoxy groups or halogen atoms, or a phenyl residue which is optionally substituted as mentioned above, for example, by aliphatic hydrocarbon residues, such as lower alkyl groups, or etherified or esterified hydroxyl groups, such as lower alkoxy groups or halogen atoms, or nitro groups. Particularly valuable are the α-(tri-$R_x$-phosphoranylidene)-α-(2-carbo-lower alkoxy-3,3-dimethyl-7-oxo-4-thia-2,6-diaza-6-bicyclo[3,2,0]heptyl)-acetic acid lower alkyl esters, in which the lower alkyl residue of the ester grouping optionally possesses one or more halogen atoms, preferably in the 2-position, and which primarily represents the tert.-butyl or 2,2,2-trichloroethyl residue, while the carbo-lower alkoxy residue in the 2-position preferably represents the carbo-tert.-butyloxy residue, and $R_x$ stands for a lower alkyl group or the phenyl group.

The compounds of the formula B can be obtained, when a reactive ester of an α-hydroxy-2-oxo-1-azetidine-methanecarboxylic acid ester of formula A is reacted with a phosphine compound of the formula

(IV)

and if necessary, a phosphonium salt compound obtainable as an intermediate product is converted to the corresponding phosphorane compound, with the elements of the acid H-X being split off and, if desired, a resulting isomer mixture is resolved into the individual isomers.

In the starting material of formula A, a group X primarily represents a halogen, especially a chlorine or bromine, as well as an iodine atom; X can also represent an organic, primarily an aliphatic or aromatic, sulphonyloxy group, for example, an optionally substituted lower alkylsulphonyloxy, e.g. methylsulphonyloxy, ethylsulphonyloxy or 2-hydroxy-ethylsulphonyloxy group, or an optionally substituted phenylsulphonyloxy group, for example, 4-methylphenylsulphonyloxy, 4-bromophenylsulphonyloxy or 3-nitrophenylsulphonyloxy group. In the phosphine compound of formula IV, the residues $R_a$, $R_b$ and $R_c$ have the above-mentioned significance and primarily represent optionally substituted lower alkyl or phenyl residues, for example, n-butyl or phenyl groups.

The above reaction is preferably performed in the presence of a suitable inert solvent, such as an aliphatic, cycloaliphatic or aromatic hydrocarbon, such as hexane, cyclohexane, benzene or toluene, or of an ether, such as dioxane, tetrahydrofuran or diethylene glycol dimethyl ether, or a solvent mixture. If necessary, the process is carried out while cooling or heating and/or in the atmosphere of an inert gas such as nitrogen.

Usually, a phosphonium salt compound of the formula

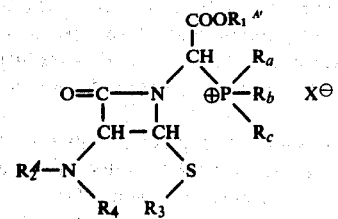

formed an an intermediate loses the elements of the acid H-X spontaneously; if necessary, the phosphonium salt compound can be decomposed by treatment with a weak base, such as an organic base, for example, diisopropylethylamine or pyridine.

The invention is described in more detail in the examples below. Temperatures are given in degrees centigrade.

EXAMPLE 1

A solutin of 3 g of 2-carbo-tert.-butyloxy-3,3-dimethyl-4-thia-2,6-diaza-bicyclo[3,2,0]heptan-7-one in 23.3 ml of dry dioxane is mixed with 5.2 g of glyoxylic acid 2,2,2-trichloroethyl ester hydrate; the reaction vessel is closed and heated for 7 hours at 95° bath temperature. The slightly yellowish, clear reaction solution is diluted with 150 ml of benzene and washed three times with 150 ml of water at a time, in the course of which resulting emulsions can be broken in a simple manner by adding 20 ml of a concentrated aqueous solution of sodium chloride. The combined aqueous solutions are washed with 150 ml of benzene; the combined organic solutions are dried with sodium sulphate and evaporated under reduced pressure. The viscous residue is dissolved in 60 ml of a 3:1-mixture of pentane and ether, whereupon the higher-melting isomer of the α-(2-carbo-tert.-butyloxy-3,3-dimethyl-7-oxo-4-thia-2,6-diaza-6-bicyclo[3,2,0]heptyl)-α-hydroxy-acetic acid 2,2,2-trichloroethyl ester of the formula

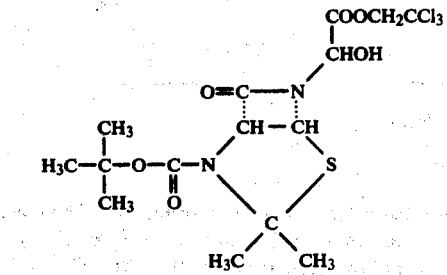

crystallises in prisms, which are filtered off when needle-shaped crystals begin to appear, m.p. 141°-146°; analytical sample: m.p. 146°-147°; $[\alpha]_D^{20} = -307° \pm 1°$ (c=0.938 in chloroform); infrared absorption spectrum (in methylene chloride): characteristic bands at 2.7μ, 5.6μ, 5.68μ, 5.85μ, 7.32μ, 8.65μ and 9.4μ.

The clear filtrate is evaporated and the residue is recrystallized from 50 ml of 5:1-mixture of pentane and ether, whereupon the lower-melting isomer of the α-(2-carbo-tert.-butyloxy-3,3-dimethyl-7-oxo-4-thia-2,6-diaza-6-bicyclo[3,2,0]heptyl)-α-hydroxy-acetic acid 2,2,2-trichloroethyl ester is obtained which melts in colourless needles at 125°-129°; analytical sample: m.p. 126°-129°; $[\alpha]_D = -187° \pm 2°$ (c=0.625 in chloroform); infrared adsorption spectrum (in methylene chloride);

characteristic bands at 2.8μ, 5.6μ, 5.84μ, 7.3μ and 7.36μ.

After 2 days, additional crystalline material is obtained from the mother liquor and after recrystallisation from a 3:1-mixture of pentane and ether, this material, in the form of prisms, melts at 140°-145° and is identical with the higher boiling isomer. A further quantity of the needle-shaped lower-melting isomer, m.p. 127°-131°, is obtained from the filtrate.

EXAMPLE 2

A mixture of 5 g of 2-carbo-tert.-butyloxy-3,3-dimethyl-4-thia-2,6-diaza-bicyclo[3,2,0]heptan-7-one and 5.5 g of glyoxylic acid tert.-butyl ester hydrate in 40 ml of dioxane is stirred for 13 ½ hours at 95° in a closed vessel and then evaporated. The residue is dissolved in 1000 ml of pentane, washed three times with 500 ml of water and once with 200 ml of a saturated aqueous sodium chloride solution, dried over dry sodium sulphate and evaporated. An approximately 50:50-mixture of the two isomers of α-(2-carbo-tert.-butyloxy-3,3-dimethyl-7-oxo-4-thia-2,6-diaza-6-bicyclo[3,2,0]heptyl)-α-hydroxy-acetic acid tert.-butyl ester of the formula

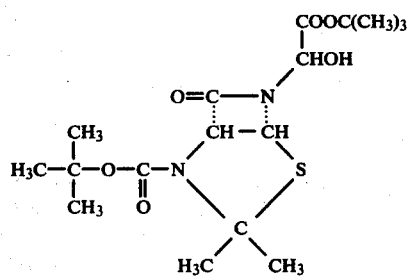

is thus obtained. 0.9 g of the resultng mixture is crystallised from pentane and recrystallised from a mixture of ether and pentane, whereupon one isomer of the above compound, m.p. 134°-137°, is obtained; $[\alpha]_D = -365° \pm 1°$ (c= 1.102 in chloroform); thin layer chromatogram: RF=0.49 in a 1:1-mixture of benzene and ethyl acetate; infra-red absorption spectrum (in methylene chloride): characteristic bands at 2.94μ, 5.62μ, 5.77μ and 5.85μ. EXAMPLE 3

A mixture of 0.05 g of the lower-melting isomer of α-(2-carbo-tert.-butyloxy-3,3-dimethyl-7-oxo-4-thia-2,6-diaza-6-bicyclo[3,2,0]heptyl)-α-hydroxy-acetic acid 2,2,2-trichloroethyl ester (Example 1) in trifluoroacetic acid is kept for 5 minutes at 20° and is then evaporated together with toluene. The residue is dissolved in methylene chloride, and the solution is washed with an aqueous sodium hydrogen carbonate solution, dried over sodium sulphate and evaporated. The residue is crystallised from hexane and the α-(3,3-dimethyl-7-oxo-4-thia-2,6-diaza-6-bicyclo[3,2,0]heptyl)-α-hydroxy-acetic acid 2,2,2-trichloroethyl ester of the formula

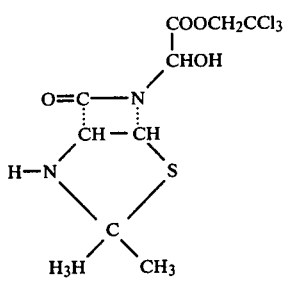

is obtained; m.p. 125°–127°; infra-red absorption spectrum with characteristic HO-band at 2.7μ.

EXAMPLE 4

A solution of 0.05 g of the higher-melting isomer of α-(2-carbo-tert.-butyloxy-3,3-dimethyl-7-oxo-4-thia-2,6-diaza-6-bicyclo[3,2,0]heptyl)-α-hydroxy-acetic acid 2,2,2-trichloroethyl ester (Example 1) in 3 ml of distilled trifluoroacetic acid is stirred for 5 minutes and then evaporated under reduced pressure without warming. The residue is neutralized with a saturated aqueous sodium hydrogen carbonate solution and is extracted with 20 ml of methylene chloride. The organic extract is dried and evaporated; the residue is recrystallized from a mixture of methylene chloride, ether and hexane; the resulting isomer of α-(3,3-dimethyl-7-oxo-4-thia-2,6-diaza-6-bicyclo[3,2,0]heptyl)-α-hydroxy-acetic acid 2,2,2-trichloroethyl ester melts at 107°–109°; analytical sample: m.p. 108°–110°; $[\alpha]_D^{20} = -176° \pm 2°$ ($c=0.513$ in chloroform); infra-red absorption spectrum (in methylene chloride): charateristic bands at 2.87μ, 3.02μ, 5.68μ, 7.33μ and 9.08μ.

EXAMPLE 5

A solution of 0.25 g of glyoxylic acid tert.-butyl ester hydrate in 5 ml of toluene is concentrated under normal pressure to a volume of about 3 ml. After cooling to 90°, 0.069 g of 2α-isopropylmercapto-3α-N-phenyloxyacetyl-aminoazetidin-4-one is added and after 2 hours the mixture is diluted with 20 ml of benzene and washed three times with 20 ml of water at a time; the aqueous washing solutions are back-washed with 10 ml of benzene, and the combined benzene solutions are dried and evaporated. The residue is degassed at a pressure of 0.05 mm Hg; the resulting amorphous mixture of the two isomers of α-hydroxy-α-(2α-isopropylmercapto-4-oxo-3α-N-phenyloxyacetylamino-1-azetidinyl)-acetic acid tert.-butyl ester of the formula

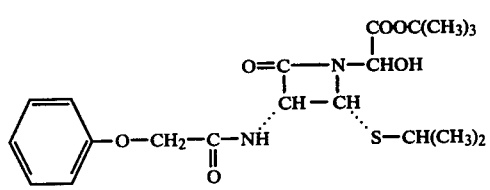

still contains a small quantity of the glyoxylic acid tert.-butyl ester hydrate; infra-red absorption spectrum (in methylene chloride); characteristic bands at 2.83μ, 2.98μ, 3.05μ, 5.65μ, 5.78μ, 5.93μ, 6.26μ, 6.60μ, 6.71μ, 7.31μ, 8.65μ and 9.23μ.

The starting material used above can be manufactured as follows:

A solution of 2.625 g of penicillin-V in 30 ml of tetrahydrofurane is mixed with 5.31 ml of a 10 ml-solution of 2 ml of triethylamine in tetrahydrofuran while stirring and cooling to −10°. 3.6 ml of a 10 ml-solution of 2 ml of chloroformic acid ethyl ester in tetrahydrofuran are then slowly added at −10° and, after completion of the addition, the mixture is stirred for 90 minutes at 10° to −5°.

The reaction mixture is treated with a solution of 0.51 g of sodium azide in 5.1 ml of water, stirred for 30 minutes at 0° to −5° and diluted with 150 ml of ice water. The mixture is extracted three times with methylene chloride; the organic extracts are washed with water, dried and evaporated at 25° and under reduced pressure. The amorphous penicillin-V azide is thus obtained as a light yellowish oil; infra-red absorption spectrum (in methylene chloride): characteristic bands at 3.04μ, 4.70μ, 5.61μ, 5.82μ (shoulder), 5.93μ, 6.26μ, 6.61μ, 6.71μ, 8.50μ and 9.40μ.

A solution of 2.468 g of penicillin-V azide in 30 ml of benzene is heated for 30 minutes to 70°. The pure 2-isocyanato-3,3-dimethyl-6-(N-phenyloxyacetylamino)-4-thia-1-azabicyclo[3,2,0]heptan-7-one can be obtained by evaporating the solution under reduced pressure; infra-red absorption spectrum (in methylene chloride): characteristic bands at 3.03μ, 4.46μ, 5.59μ, 5.93μ, 6.26μ, 6.62μ, 6.70μ, 7.53μ, 8.28μ, 8.53μ, 9.24μ and 9.40μ.

The above solution of the 2-isocyanato-3,3-dimethyl-6-(N-phenyloxyacetyl-amino)-4-thia-azabicyclo[3,2,0-]heptan-7-one is mixed with 3.4ml of a 10 ml-solution of 2 ml of 2,2,2-trichloroethanol in benzene and the reaction mixture is kept for 95 minutes at 70°. The solvent is removed under reduced pressure and the residue is purified on 40 ml of acid-washed silica gel (column). By-products are eluted with 300 ml of benzene and 300 ml of a 19:1-mixture of benzene and ethyl acetate, and the pure 2-(N-carbo-2,2,2-trichloroethoxy-amino)-3,3-dimethyl-6-(N-phenyloxyacetyl-amino)-4-thia-1-azabicyclo[3,2,0]heptan-7-one of the formula

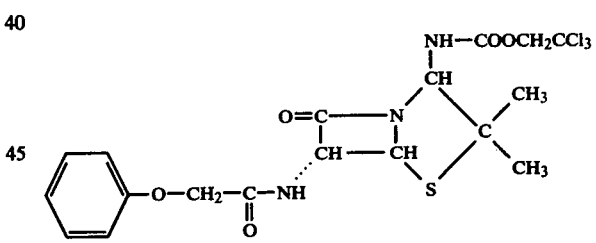

is eluted with 960 ml of a 9:1-mixture of benzene and ethyl acetate. After recrystallization from a mixture of ether and pentane, the product melts at 169°–171° (with decomposition); $[\alpha]_D^{20} = +83°$ ($c=1.015$ in chloroform); thin layer chromatogram (silica gel): RF=0.5 in a 1:1-mixture of benzene and ethyl acetate; infra-red absorption spectrum (in methylene chloride): characteristic bands at 3.05μ, 5.62μ, 5.77μ, 5.93μ, 6.27μ, 6.62μ, 6.70μ, 8.30μ, 9.23μ and 9.50μ.

The last fractions eluted with a 9:1-mixture of benzene and ethyl acetate contain a small quantity of the product which is isomeric in the 2-position with the above compound.

A solution of 3 g of crystalline 2-(N-carbo-2,2,2-trichloroethoxy-amino)-3,3-dimethyl-6-(N-phenyloxyacetylamino)-4-thia-1-azabicyclo[3,2,0]heptan-7-one in 65 ml of 90% aqueous acetic acid and 30 ml of dimethylformamide is mixed over the course of 20 minutes with 32.6 g of zinc dust while cooling with ice and then stirred for 20 minutes. The excess zinc is filtered off and the filtered residue is washed with benzene; the filtrate is diluted with 450 ml of benzene, washed with a saturated aqueous sodium chloride solution and water, dried and evaporated under reduced pressure. The residue is purified on a column of 45 g of acid-washed silica gel. Apolar products are eluted with 100 ml of benzene and 400 ml of a 9:1-mixture of benzene and ethyl acetate and starting material with 100 ml of a 4:1-mixture of benzene and ethyl acetate. Using a further 500 ml of the 4:1-mixture of benzene and ethyl acetate and 200 ml of a 2:1-mixture of benzene and ethyl acetate, the 3,3-dimethyl-2-hydroxy-6-(N-phenyloxyacetyl-amino)-4-thia-1-azabicyclo[3,2,0]-heptan-7-one of the formula

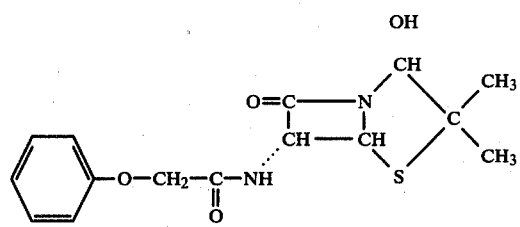

is obtained; it crystallises spontaneously as the hydrate and after trituration with water-saturated ether melts in an unsharp manner in the range of 62°–85°.

When chromatographed, but non-crystalline starting material is used and the reduction is carried out in dilute acetic acid without the addition of dimethylformamide, the pure product, m.p. 62°–70°, is obtained; thin layer chromatogram (silica gel); Rf=0.35 in a 1:1-mixture of benzene and ethyl acetate; infra-red absorption spectrum (in methylene chloride): characteristic bands at 2.93μ, 3.09μ, 5.65μ, 5.96μ, 6.29μ, 6.65μ, 6.75μ, 8.57μ, 9.27μ, 10.00μ and 11.95μ.

A solution of 0.065 g of 3,3-dimethyl-2-hydroxy-6-(N-phenyloxyacetyl-amino)-4-thia-1-azabicyclo[3,2,0]-heptan-7-one in 5 ml of benzene is treated with 0.15 g of lead tetraacetate, containing 10% of acetic acid, and the yellow solution is irradiated with a high pressure mercury vapour lamp (80 watts) in a water-cooling pyrex glass jacket. After 10 minutes the yellow colour disappears and a partially flocculant white, partially gum-like yellow, precipitate forms. The mixture is diluted with benzene, washed with water, a dilute sodium hydrogen carbonate solution and water, and evaporated under reduced pressure. The resulting 1-formyl-2-(2-acetyloxy-2-propyl-mercapto)-3-(N-phenyloxyacetyl-amino)-azeticin-4-one of the formula

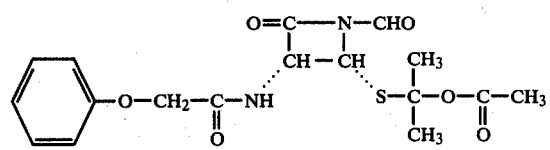

is obtained as a slightly yellowish gum-like product; infrared absorption spectrum (in methylene chloride); characteristic bands at 3.05μ, 5.56μ, 5.78μ, 5.90μ, 6.27μ, 6.62μ, 6.71μ, 7.33μ, 7.67μ, 8.92μ, 9.24μ, and 9.82μ.

A solution of 0.051 g of 1-formyl-2-(2-acetyloxy-2-propyl-mercapto)-3-(N-phenyloxyacetyl-amino)-azetidin-4-one in 3 ml of anydrous benzene is treated with 0.13 g of tristriphenyl-phosphine-rhodium chloride and boiled for 3 hours under reflux. The initially red solution turns brown, with a small quantity of a precipitate forming. After cooling, the precipitate is filtered off and the filtrate is evaporated under reduced pressure. The residue is chromatographed on 5 g of acid-washed silica gel, with fractions of 5 ml each being collected. The elution is carried out with 10 ml of benzene, 30 ml of a 9:1-, 25 ml of a 4:1- and 10 ml of a 1:1-mixture of benzene and ethyl acetate and then with 25 ml of ethyl acetate. Fractions 2-6 yield a rhodium complex having a strong CO-absorption at 5.18μ in the infra-red absorption spectrum. A small quantity of 1-formyl-2-isopropenylmercapto-3-(N-phenyloxyacetyl-amino)-azetidin-4-one can be isolated from fractions 10–12, while fractions 15–17 yield the 2-isopropenylmercapto-3-(N-phenyloxyacetyl-amino)-azetidin-4-one of the formula

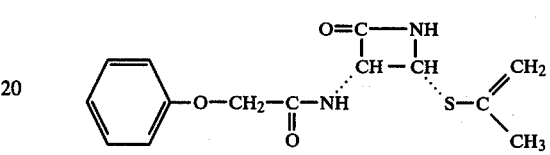

in an amorphous form. The product is obtained in crystalline form when the solution of the eluate is filtered through 0.5 g of acid-washed silica gel and the product is eluted with a 1:1-mixture of benzene and ethyl acetate, m.p. 156°–158°; $[\alpha]_D^{20} = -70°$ ±2°(c =0.665 in chloroform); infra-red absorption spectrum (in methylene chloride): characteristic bands at 3.07μ, 5.65μ, 5.96μ, 6.29μ, 6.59μ, 6.74μ, 8.19μ, 9.25μ and 9.92μ.

A solution of 0.08 g of 2α-isopropenylmercapto-3-(N-phenyloxyacetyl-amino)-azetidin-4-one in 10 ml of ethyl acetate is mixed with 0.1 g of a 10% palladium-on-characoal catalyst and the mixture is stirred for 45 minutes in a hydrogen atmosphere and then filtered. The filtrate is evaporated and the crystalline residue is recrystallised from a mixture of methylene chloride and ether. The 2α-isopropylmercapto-3(N-phenyloxyacetyl-amino)-azetidin-4-one of the formula

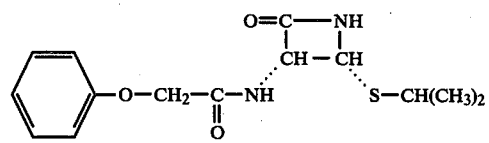

is thus obtained, m.p. 128°–130° and 143° (double melting point); $[\alpha]_D^{20} = -48° \pm 1°$(c =0.785 in chloroform); infra-red absorption spectrum (in methylene chloride); characteristic bands at 3.05μ, 5.63μ, 5.93μ, 6.26μ, 6.58μ, 6.70μ, 8.15μ, 9.21μ and 9.41μ.

EXAMPLE 6

By concentrating a solution of 0.414 g of glyoxylic acid tert.-butyl ester hydrate in 5 ml of toluene to a volume of 3 ml the anydrous compound is obtained; the solution is treated at 90° with 0.128 g 2α-isopropenyl-mercapto-3α-(N-phenyloxyacetyl-amino)-azetidin-4-one. The mixture is kept at 90° for three hours and after cooling is treated with methylene chloride, washed with water, dried and evaporated under reduced pressure. The residue is chromatographed on 10 g of acid-washed silica gel. The amorphous mixture of the two isomers of α-hydroxy-α-[2α-isopropenylmercapto-4-oxo-3α-(N-phenyloxyacetyl-amino)-1-azetidinyl]-acetic acid tert.-butyl ester of the formula

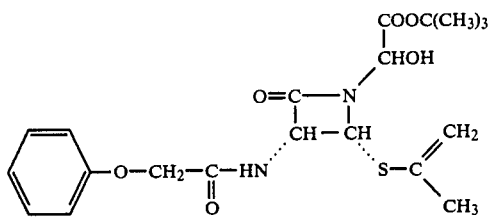

is eluted with a 4:1-mixture of benzene and ethyl acetate, infrared absorption spectrum (in methylene chloride); characteristic bands at 2.95μ, 3.03μ, 5.62μ, 5.78μ, 5.91μ, 6.24μ, 6.60μ, 7.25μ, 8.62μ and 9.22μ.

The compounds which can be manufactured according to the above process can be further processed as follows:

EXAMPLE 7

A solution of 1.84 g of the higher-melting isomer of α-(2-carbo-tert.-butyloxy-3,3-dimethyl-7-oxo-4-thia-2,6-diaza-6-bicyclo[3,2,0,]heptyl)-α-hydroxy-acetic acid 2,2,2-trichloroethyl ester in 20 ml of a 1:4-mixture of dry dioxane and tetrahydrofuran is mixed with 12 ml of a freshly prepared 1 molar solution of triethylamine in dioxane. The mixture is cooled to −15° and treated dropwise with 8 ml of a freshly prepared 1 molar solution of thionyl chloride in dioxane, with exclusion of atmospheric moisture, and is then stirred for 5 minutes at −15°. After warming to room temperature and 10 minutes stirring at 20°, the mixture is diluted with 60 ml of toluene and filtered through a glass filter. The clear filtrate is evaporated under reduced pressure and at a bath temperature of below 45°. The residue is dried for 2 hours at 25°/0.01 mm Hg and is then triturated three times with 60 ml at a time of boiling pentane; the solution is stirred for 10 minutes with 0.3 g of an active charcoal preparation and is filtered through a glass filter. After evaporation, the residue is crystallised from pentane; the resulting α-(2-carbo-tert.-butyloxy-3,3-dimethyl-7-oxo-4-thia-2,6-diaza-6-bicyclo[3,2,0]heptyl)-α-chloroacetic acid 2,2,2-trichloroethyl ester of the formula

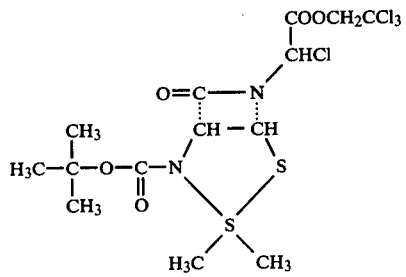

melts at 131°–136° after repeated recrystallisations from pentane; analytical sample: m.p. 130°–131°; [α]$_D^{20}$ = −307° ±1° (c = 0.991 in chloroform); thin layer chromatogram (silicagel): Rf = 0.73 (streaking) in 1:1 mixture of benzene and ethylacetate; infra-red absorption spectrum (in methylene chloride): characteristic bands at 5.60μ, 5.64μ and 5.85μ.

EXAMPLE 8

A mixture of 12 g of the so-called "polystrene-Hunig base" (manufactured by warming a mixture of 100 g of chloromethylpolystyrene [J. Am. Chem. Soc. 85, 2149 (1963)], 500 ml of benzene, 200 ml of methanol and 100 ml of diisopropylamine to 150° while shaking, filtering, washing with 1000 ml of methanol, 1000 ml of a 3:1-mixture of dioxane and triethylamine, 1000 ml of methanol, 1000 ml of dioxane and 1000 ml of methanol and drying for 16 hours at 100°/10 mm Hg; the product neutralises 1.55 milliequivalents of hydrochloric acid per gram in a 2:1-mixture of dioxane and water) in 50 ml of a 1:1-mixture of dioxane and tetrahydrofuran is stirred for 30 minutes, and is then treated with a solution of 1.84 g of the higher-melting isomer of α-(2-carbo-tert.-butyloxy-3,3-dimethyl-7-oxo-4-thia-2,6-diaza-6-bicyclo[3,2,0].heptyl)-α-hydroxy-acetic acid 2,2,2-trichloroethyl ester in 5 ml of a 1:1 -mixture of dioxane and tetrahydrofuran. After cooling the mixture to −15° while stirring, 8 ml of a freshly prepared 1 molar solution of thionyl chloride in dioxane are added dropwise; the mixture is stirred for 10 minutes at −15° and then for 90 minutes at 25°. After filtering, the filter residue is washed three times with 30 ml of dioxane at a time; the combined filtrates are evaporated at a bath temperature below 45°. The 60-(2-carbo-tert.-butyloxy-3,3-dimethyl-7-oxo-4-thia-2,6-diaza-6-bicyclo[3,2,0]heptyl)-α-chloroacetic acid 2,2,2-trichloroethyl ester is obtained as a viscous residue, which, after recrystallisation from 30 ml of pentane, melts at 130°–131°.

EXAMPLE 9

A mixture of 6 g of a 1:1-mixture of the isomers of α-(2-carbo-tert.-butyloxy-3,3-dimethyl-7-oxo-4-thia-2,6-diaza-6-bicyclo[3,2,0]heptyl)-α-hydroxy-acetic acid tert.-butyl ester and 10.5 g of the so-called "polystyrene-Hunig base" (see example 8) in a 1:1-mixture of dioxane and tetrahydrofuran is stirred for 20 minutes. After cooling, the mixture is treated dropwise over the course of 20 minutes with a solution of 6 g of thionyl chloride in 50 ml of dioxane and is stirred for 140 minutes at 20° and then filtered. The filtrate is evaporated, the residue is taken up in 200 ml of pentane and the solution is treated with 1 g of an active charcoal preparation and then filtered. An approximately 1:1-mixture of the isomers of α-(2-carbo-tert.-butyloxy-3,3-dimethyl-7-oxo-4-thia-2,6-diaza-6-bicyclo[3,2,0]heptyl)-α-chloro-acetic acid tert.-butyl ester of the formula

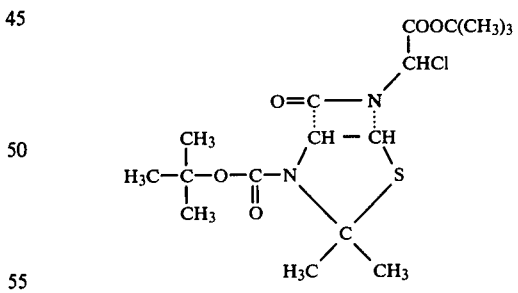

is thus obtained and used without purification.

EXAMPLE 10

A solution of 0.165 g of α-(2-carbo-tert.-butyloxy-3,3-dimethyl-7-oxo-4-thia-2,6-diaza-6-bicyclo[3,2,0]-heptyl)-α-chloro-acetic acid 2,2,2-trichloroethyl ester in 30 ml of dry ether is mixed with 0.22 g of dry lithium bromide and the suspension is stirred for 150 minutes at 25°. The filtered solution is diluted with 20 ml of pentane and then again filtered and evaporated. The residue is triturated with 20 ml of a 9:1-mixture of boiling pentane and ether and filtered and the clear filtrate is evaporated. The resulting α-(2-carbo-tert.-butyloxy-3,3-dimethyyl-7-oxo-4-thia-2,6-diaza-6-bicyclo [3,2,0]heptyl)-α-bromo-acetic acid 2,2,2-trichloroethyl ester of the formula

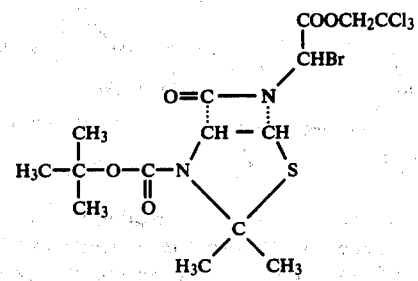

melts at 119°-120° (with decomposition) after crystallisation from pentane.

EXAMPLE 11

A solution of 0.115 g of the crude mixture of the isomers of α-hydroxy-α-(2α-isopropylmercapto-4-oxo-3=-N-phenyloxyacetylamino-1-azetidinyl)-acetic acid tert.-butyl ester (about 0.1 g of the two epimers) in 2.4 ml of anhydrous dioxane is mixed with 0.1 g of "polystyrene-Hunig base" and cooled to 0° while stirring. 0.06 of thionyl chloride in 0.5 ml of dioxane are added and the mixture is stirred for a further 2¼ hours at room temperature and filtered; the filter residue is washed with dioxane and the filtrate is evaporated under reduced pressure. The residue contains the mixture of the isomers of the α-chloro-α-(2α-isopropylmercapto-4-oxo-3α-N-phenyloxyacetylamino-1-azetidinyl)-acetic acid tert.-butyl ester of the formula

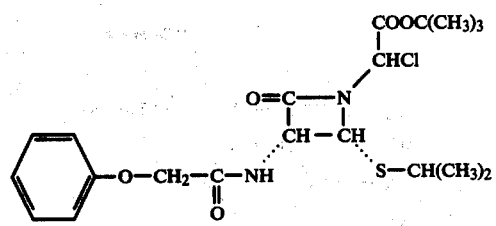

which shows the following characteristic bands in the infra-red absorption spectrum (in methylene chloride): 3.05μ, 5.63μ, 5.75μ, 5.93μ, 6.25μ, 6.70μ, 7.30μ and 8.70μ.

EXAMPLE 12

A solution of 11.3 g of a crude mixture of the isomers of α-(2-carbo-tert.-butyloxy-3,3-dimethyl-7-oxo-4-thia-2,6-diaza-6-bicyclo[3,2,0]heptyl)-α-chloro-acetic acid tert.-butyl ester in 150 ml of absolute dioxane is mixed with 11.4 g of triphenylphoshine and 10.8 g of "polystyrene-Hunig base" or diisopropylaminomethyl-polystyrene, stirred for 17 hours at 55° under a nitrogen atmosphere and then cooled and filtered through a glass filter. The filter residue is washed with 100 ml of benzene, and the filtrate is evaporated under water jet pump vacuum; the residue is dried under a high vacuum, dissolved in 100 ml of a 9:1-mixture of hexane and ethyl acetate and chromatographed on a column (height 48 cm; diameter 6 cm) of acid-washed silica gel. Triphenylphosphine and a small amount of triphenylphosphinesulphide are eluted with 2000 ml of a 3:1-mixture of hexane and ethyl acetate, and the α-(2-carbo-tert.-butyloxy-3,3-dimethyl-7-oxo-4-thia-2,6-diaza-6-bicyclo[3,2,0]-heptyl)-α-(triphenylphosphoranylidene)-acetic acid tert.-butyl ester of the formula

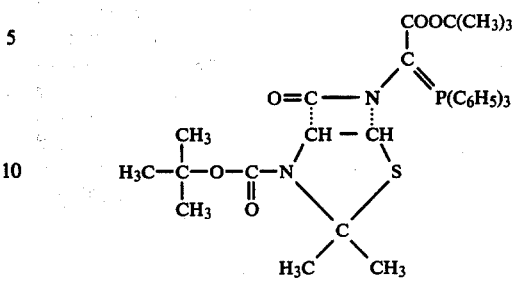

is eluted with an additional 4000 ml of the 3:1-mixture of hexane and ethyl acetate; a further quantity of the impure product can be obtained with 1500 ml of the same solvent mixture. The product has an Rf-value of 0.5 in a thin layer chromatogram (silica gel; system: 1:1-mixture of benzene and ethyl acetate) and crystallises from a mixture of ether and pentane, m.p. 121°-122°; $[\alpha]_D = -219° \pm 1°$ (c = 1.145 in chloroform); ultra-violet absorption spectrum (in ethanol)-$\lambda_{max}$ = 225mμ (ε = 30,000) and 260mμ (ε = 5400); infra-red absorption spectrum (in methylene chloride): characteristic bands at 5.76μ, 5.80μ (shoulder), 5.97μ, 6.05μ (shoulder) and 6.17μ. A further quantity of the product can be isolated from the mother liquor by crystallisation in an ether-pentane mixture.

EXAMPLE 13

A solution of 0.1 g of α-(2-carbo-tert.-butyloxy-3,3-dimethyl-7-oxo-4-thia-2,6-diaza-6-bicyclo[3,2,0]heptyl)-α-chloroacetyl acid 2,2,2-trichloroethyl ester in 3 ml of dry benzene (after treatment with sodium and filtration through aluminum oxide, neutral, activity I) is treated with 0.072 g of freshly distilled tri-n-butyl-phosphine and the mixture is stirred for 25 hours at room temperature. The resulting product is chromatographed on silica gel, whereupon the α-(2-carbo-tert.-butyloxy-3,3-dimethyl-7-oxo-4-thia-2,6-diaza-6-bicyclo[3,2,0]heptyl)-α-(tri-n-butyl-phosphoranylidene)-acetic acid 2,2,2-trichloroethyl ester of the formula

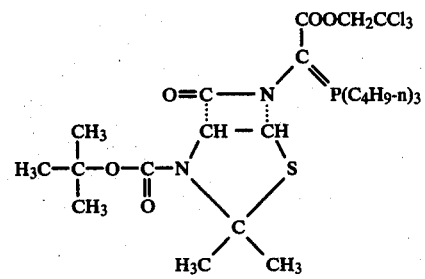

is obtained by means of a 9:1-mixture of benzene and ethyl acetate and used without further purification.

EXAMPLE 14

A mixture of 0.735 g of "polystyrene-Hunig base" in 10 ml of dioxane (treated with neutral aluminum oxide, activity I) is reacted with 0.34 g of triphenylphosphine (recrystallised from hexane) and then with 0.5 g of α-(2-carbo-tert.-butyloxy-3,3-dimethyl-7-oxo-4-thia-2,6-diaza-6-bicyclo[3,2,0]heptyl)-α-chloroacetic acid 2,2,2-trichloroethyl ester and is stirred for 17 hours at 60° under a nitrogen atmosphere. The mixture is filtered through a glass filter and the filter residue is twice washed with 5 ml of methylene chloride at a time and once with 5 ml of benzene. The filtrate is evaporated to dryness under reduced pressure and the residue is chromatographed on silica gel. Triphenylphosphine, starting material and dehalogenated starting material are eluted with benzene and with a 19:1-mixture of benzene and ethyl acetate. The desired α-(2-carbo-tert.-butyloxy-3,3-dimethyl-7-oxo-4-thia-2,6-diaza-6-bicyclo [3,2,0]heptyl)-α-(triphenylphosphoranylidene)-acetic acid 2,2,2-trichloroethyl ester of the formula

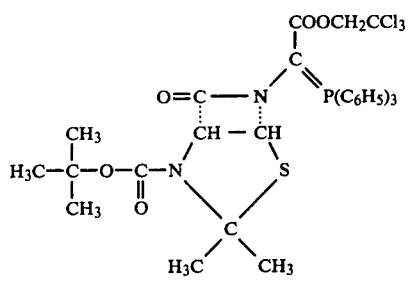

is obtained with a 9:1-mixture of benzene and ethyl acetate, in an oily form; after two crystallisations from a methylene chloride-pentane mixture, the material melts at 205°; $[\alpha]_D^{20} = -192° \pm 1°$ ($c = 1.054$ in chloroform); thin layer chromatogram (silica gel): Rf~0.54 in the system benzene-ethyl acetate (3:1); ultraviolet absorption spectrum (in ethanol):$\lambda_{max} = 225$mμ ($\epsilon = 30,100$) and 265 mμ ($\epsilon = 5760$); infra-red absorption spectrum (in methylene chloride): characteristic bands at 5.65μ, 5.85μ and 6.10μ. Polar products are eluted by means of a 4:1-mixture of benzene and ethyl acetate.

EXAMPLE 15

A mixture of 0.104 g of α-(2-carbo-tert.-butyloxy-3,3-dimethyl-7-oxo-4-thia-2,6-diaza-6-bicyclo[3,2,0]heptyl)-α-bromoacetic acid 2,2,2,-trichloroethyl ester and triphenylphosphine (1.3 equivalents) in 0.2 ml of benzene at 25° yields at colourless precipitate within 20 minutes. After one hour, the precipitate is filtered off, washed 4 times with 0.5 ml of a 1:1-mixture of benzene and hexane and dried. The α-(2-carbo-tert.-butyloxy-3,3-dimethyl-7-oxo-4-thia-2,6-diaza-6-bicyclo[3,2,0]heptyl)-α-(triphenylphosphonium)-acetic acid 2,2,2-trichloroethyl ester bromide is thus obtained, which after treatment with an aqueous sodium carbonate solution yields the crude α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid 2,2,2-trichloroethyl ester, m.p. 201°-202° after crystallisation from hexane.

EXAMPLE 16

A solution of 0.115 g of the crude mixture of the isomers of α-chloro-α-(2α-isopropylmercapto-4-oxo-3α-N-phenyloxyacetylamino-1-azetidinyl)-acetic acid tert.-butyl ester in 2 ml of dioxane is mixed with 0.12 g of triphenylphosphine and 0.11 g of "polystyrene-Hunig base" and the mixture is stirred for 16 hours at 55°, then filtered. The filter residue is washed with benzene and the filtrate is evaporated to dryness under reduced pressure. The residue is chromatographed on 5 g of acid-washed silica gel. The excess triphenylphosphine is eluted with 40 ml of benzene; the desired α-(2α-isopropylmercapto-4-oxo-3α-N-phenyloxyacetylamino-1-azetidinyl)-α-triphenylphosphoranylideneacetic acid tert.-butyl ester of the formula

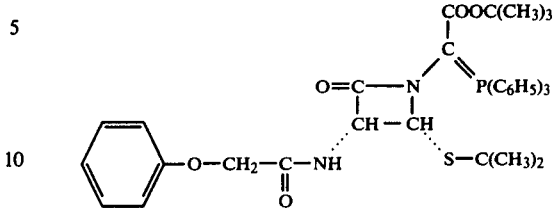

is obtained as a colourless oil by elution with a 1:1-mixture of benzene and ethyl acetate, as well as with ethyl acetate; infra-red absorption spectrum (in methylene chloride): characteristic bands at 3.05μ, 5.71μ, 5.94μ, 6.17μ, 6.58μ, 6.72μ, 7.34μ, 8.60μ and 9.03μ.

EXAMPLE 17

A solution of 0.301 g of α-(2-carbo-tert.-butyloxy-3,3-dimethyl-7-oxo-4-thia-2,6-diaza-6-bicyclo[3,2,0]-heptyl)-α-(tripenylphosphanylidene)-acetic acid 2,2,2-trichloroethyl ester and 0.3 g of liquid glyoxylic acid tert.-butyl ester (mainly in the form of the hydrate) is stirred for 22 hours at 50° and is then diluted with benzene and washed with water, dried and evaporated under reduced pressure. The crude product is taken up in benzene and is filtered through a column of 3 g of acid-washed silica gel. The pure mixture of the isomers of α-(2-carbo-tert.-butyloxy-3,3-dimethyl-7-oxo-4-thia-2,6-diaza-6-bicyclo[3,2,0]heptyl)-α-(carbo-tert.-butyloxy-methylene)-acetic acid 2,2,2-trichloroethyl ester of the formula

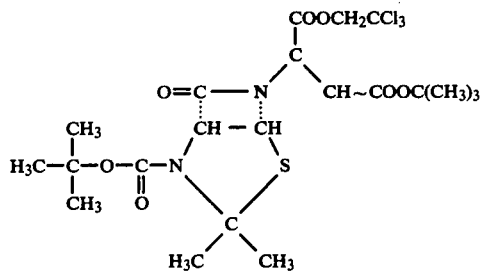

is obtained with 90 ml of benzene. Crystallisation from ether yields the isomer A which after renewed recrystallisation melts at 189°; $[\alpha]_D^{20} = -329° \pm 2°$ (c = 0.558 in chloroform); thin layer chromatogram (silica gel): Rf~0.64 in a 3:1-mixture of benzene and ethyl acetate; ultraviolet absorption spectrum (in ethanol):$\lambda_{max} = 270$ mμ ($\epsilon = 17,600$); infra-red absorption spectrum (in methylene chloride): characteristic bands at 5.61μ, 5.68μ(shoulder), 5.75μ(shoulder), 5.87μ, 6.17μ, 7.27μ, 7.37μ, 8.70μ and 9.32μ. Crystallisation of the mother liquor residue from an ether-pentane mixture yields a crystalline isomer mixture, from which isomer B can be removed by washing out with cold ether; isomer B is obtained in fine needles from the filtrate after evaporation and crystallisation from an ether-pentane mixture, m.p. 119°-120°; $[\alpha]_D^{20} = -363° \pm 1°$ (c = 1.213 in chloroform); thin layer chromatogram (silica gel): Rf~0.64 in a 3:1-mixture of benzeneethyl acetate; ultra-violet absorption spectrum (in ethanol): $\lambda_{max}$ 279mμ ($\epsilon = 8900$); infra-red absorption spectrum (in methylene chloride): characteristic bands at 5.62μ, 5.75μ, 5.87μ, 6.15μ, 7.31μ, 8.65μ, 9.05μ and 9.30μ.

The above reaction can also be carried out as follows: A solution of 5.04 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid 2,2,2-trichloroethyl ester in 15 ml of absolute toluene, prepared at 60°, is mixed with a solution of 4.5 g of glyoxylic acid tert.-butyl ester in 10 ml of absolute toluene while stirring in a nitrogen atmosphere, and is heated for 15 hours at 60°. After evaporation of the solvent under reduced pressure, the oily residue in benzene is filtered through a column (diameter: 3 cm; hight 32 cm) of 100 g of acid-washed silica gel. The pure mixture of isomers A and B of α-(2-carbo-tert.-butyloxy-3,3-dimethyl-7-oxo-4-thia-2,6-diaza-6-bicyclo[3,2,0]heptyl)-α-carbo-tert.-butyloxymethylene)-acetic acid 2,2,2-trichloroethyl ester is obtained with 500 ml of benzene and an impure isomer mixture with a further 750 ml of benzene. On crystallisation according to the process described above the pure product yields the pure isomer A, m.p. 191°; and the mother liquor yields the pure isomer B, m.p. 120°-121°; a further quantity of the isomer B can be obtained from the impure mixture.

EXAMPLE 18

A mixture of 0.035 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid 2,2,2-trichloroethyl ester and 0.036 g of glyoxylic acid 2,2,2-trichloroethyl ester hydrate in 0.5 ml of toluene is heated at 50° for 5 hours and under a nitrogen atmosphere. After diluting with benzene and washing with water, a residue is obtained from the organic solution which is purified by filtration through 0.7 g of acid-washed silica gel. The mixture of the two isomers of α-(2-carbo-tert.-butyloxy-3,3-dimethyl-7-oxo-4-thia-2,6-diaza-6-bicyclo[3,2,0]heptyl)-α-(carbo-2,2,2-trichloroethoxymethylene)-acetic acid 2,2,2-trichlorethyl ester of the formula

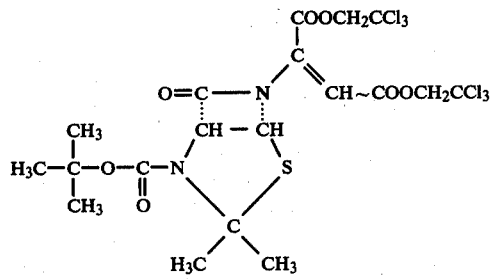

is obtained by elution with 20 ml of benzene; thin-layer chromatogram (silica gel): Rf~0.7 in a 3:1-mixture of benzene and ethyl acetate. On crystallisation from an ether-pentane mixture, an isomer is obtained as a crystalline product which melts at 176°-177° and very probably has the configuration of maleic acid.

EXAMPLE 19

A solution of 0.212 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid 2,2,2-trichloroethyl ester in 0.5 g of ethylene glycol dimethyl ether is reacted in a sealed glass tube with glyoxylic acid ethyl ester-hemiethyl acetal for 17 hours at 60°. The mixture is then diluted with 1 ml of xylene and evaporated under reduced pressure. The residue is chromatographed on silica gel (column of 1.8 cm diameter and 20 cm length), elution being carried out with a 95:5-mixture of benzene and ethyl acetate. A 5:1-mixture of the two isomers of α-(2-carbo-tert.-butyloxy-3,3-dimethyl-7-oxo-4-thia-2,6-diaza-6-bicyclo[3,2,0]heptyl)-α-carbethoxymethylene)-acetic acid 2,2,2-trichloroethyl ester of the formula

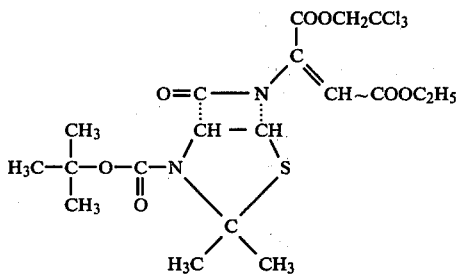

is thus obtained, which after recrystallisation from pentane, melts at 95°; ultra-violet absorption spectrum (in ethanol): $\lambda_{max} = 277$ mμ ($\epsilon = 10,550$); infra-red absorption spectrum (in methylene choride); characteristic bands at 5.65μ, 5.85μ, 5.90μ and 6.20μ.

EXAMPLE 20

A solution of 0.5 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester in 5 ml of dry dioxane is reacted for 1-¾ hours with 0.6 g of glyoxylic acid 2,2,2-trichloroethyl ester hydrate under a nitrogen atmosphere at 60°. The solvent is then removed under reduced pressure; the residue is diluted with 10 ml of benzene, whereupon the excess glyoxylic acid ester crystallises out and is filtered off. The filtrate is washed three times with 10 ml of water and the washing liquids are backwashed with benzene and the organic solutions dried over sodium sulphate and evaporated. The crude product is chromatographed on silica gel (column of 1.8 cm diameter and 15 cm hight), elution being carried out with 150 ml of benzene, 100 ml of a 49:1-mixture and 100 ml of a 19:1-mixture of benzene and ethyl acetate. A 4:1-mixture of the two isomers of α-(2-carbo-tert.-butyloxy-3,3-dimethyl-7-oxo-4-thia-2,6-diaza-6-bicyclo[3,2,0]heptyl)-α-(carbo-2,2,2-trichloroethoxymethylene)-acetic acid tert.-butyl ester of the formula

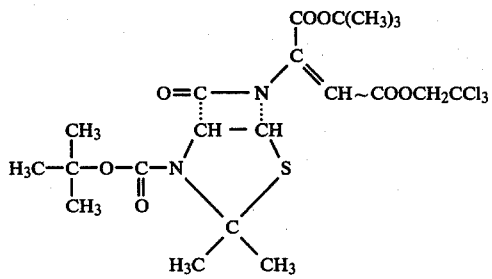

is thus obtained. From the fractions containing primarily the isomer A, the latter is obtained by crystallisation from pentane, m.p. 130°-131°; $[\alpha]_D^{20} = -371° \pm 1°$ (c = 1.061 in chloroform); thin layer chromatogram (silica gel): Rf 0.5 in a 3:1-mixture of benzene and hexane; ultra-violet absorption spectrum (in ethanol): $\lambda_{max} = 287$ mμ($\epsilon = 10,950$); infra-red absorption spectrum (in methylene chloride): characteristic bands at 5.65μ, 5.83μ, 5.90μ and 6.20μ. The other isomer shows an Rf-value of 0.3 in a thin layer chromatogram.

EXAMPLE 21

A mixture of 4 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 0.9 g of glyoxylic acid hydrate in 80 ml of absolute dioxane is kept for 3 hours at room temperature under a nitrogen atmosphere and is then evaporated under reduced pressure at a bath temperature of 45°. The residue is dissolved in 150 ml of ether and three times extracted with 40 ml of a 1N aqueous sodium carbonate solution each time. The aqueous extracts are washed with 150 ml of ether, mixed with 20 ml of a concentrated phosphate buffer solution (pH 6) and acidified to pH 6-5 with 63.2 ml of 2N aqueous sulphuric acid, and are then extracted four times with 150 ml of ether each time. The ether extracts are dried over sodium sulphate and evaorated. The mixture of the isomers of α-(2-carbo-tert.-butyloxy-3,3-dimethyl-7-oxo-4-thia-2,6-6-bicyclo[3,2,0]heptyl)-α-(carboxymethylene)-acetic acid tert.-butyl ester of the formula

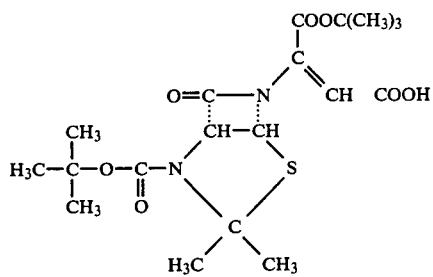

is thus obtained, which consists of about 65% of the isomer A and about 35% of the isomer B. By chromatography on acid-washed silica gel and using a 4:1-mixture of hexane and ethyl acetate the isomer A is first eluted; m.p. 130° after three crystallisations from pentane; $[\alpha]_D^{20} = -457° \pm 1°$ (c = 1 in chloroform); thin layer chromatography Rf=0.40 (silica gel; system toluene: acetic acid: water 5:4:1); ultra-violet absorption spectrum (in ethanol):$\lambda_{max}$ 277 mμ ($\epsilon$= 8850); infra-red absorption spectrum (in methylene chloride): characteristic bands at 5.65μ, 5.80–5.95μ and 6.25μ; then the isomer B, which after three crystallisations from pentane melts at 177°; $[\alpha]_D^{20} = -431° \pm 1°$ (c = 1.041 in chloroform); thin layer chromatographyl (silica gel; system toluene: acetic acid: water 5:4:1): Rf =0.47; ultra-violet absorption spectrum (in ethanol): $\lambda_{max}$ 270 mμ ($\epsilon$= 17,000); infra-red absorption spectrum (in methylene chloride): characteristic bands at 5.65μ, 5,80–5,95μ and 6.25μ (strong).

EXAMPLE 22

A solution of 2 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 0.7 g of benzyglyoxal (in enol form) in 30 ml of dry toluene is heated for 23 hours at 80° (bath temperature) in a nitrogen atmosphere, and is then mixed with a further quantity of 0.2 g of benzylglyoxal; the mixture is heated for 22 hours at 80°. The solvent is removed under reduced pressure and the viscous residue is chromatographed on a column of 60 g of acid-washed silica gel. The excess benzylglyoxal is eluted with 450 ml of benzene; a mixture of the isomers of α-(2-carbo-tert.-butyloxy-3,3-dimethyl-7-oxo-4-thia-2,6-diaza-6-bicyclo[3,2,0]heptyl)-α-(phenylactylmethylene)-acetic acid tert.-butyl ester of the formula

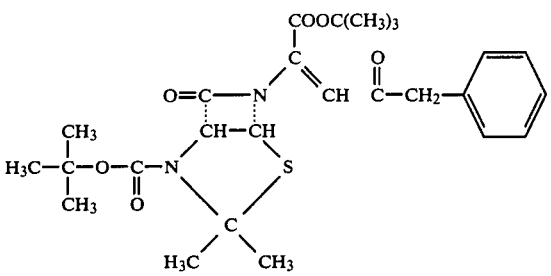

is eluted with 250 ml (10 fractions) of a 95:5-mixture of benzene and ethyl acetate, and a polar material is eluted with a further quantity of the same solvent mixture.

The above mixture of isomers is again chromatographed on 60 g of acid-washed silica gel, elution being carried out with a 99:1-mixture of benzene and ethyl acetate. A product consisting mainly of benzylglyoxal is obtained as the forerun, and then a fraction I consisting mainly of isomer A is obtained with 125 ml, a fraction II consisting of a mixture of both isomers with 250 ml, and a fraction III consisting mainly of isomer B with 300 ml. The above three fractions are recrystallised from hexane, whereupon fraction I yields isomer A; m.p. 109°–110°; $[\alpha]_D^{20} = -452° \pm 1°$ (c = 1 in chloroform); thin layer chromatogram: Rf = 0.49 (silica gel; system hexane:ethyl acetate, 2:1); ultra-violet absorption spectrum:$\lambda_{max}$ 297 mμ ($\epsilon$= 11,000) (in ethanol), 337 mμ(in potassium hydroxide/ethanol) and 337 mμ (on acidifying a basic solution in ethanol); infra-red absorption spectrum (in methylene chloride): characteristic bands at 5.63μ, 5.83μ (shoulder), 5.85–5.95μ and 6.29μ; and fractions II and III yield isomer B; m.p. 157°–158°; $[\alpha]_D^{20} = -363° \pm 0.7°$ (c = 1 in chloroform); thin layer chromatogram: Rf = 0.42 (silica gel; system hexane:ethyl acetate, 2:1); ultra-violet absorption spectrum:$\lambda_{max}$ 294 mμ ($\epsilon$= 19,300) (in ethanol), 335 mμ (potassium hydroxide/ethanol) and 335 mμ (on acidifying a basic solution in ethanol) infra-red absorption spectrum (in methylene chloride): characteristic bands at 5.63μ, 5.80μ (shoulder), 5.84–5.96μ and 6.34μ. Further quantities of the two isomers can be isolated from the mother liquors in the same manner.

EXAMPLE 23

A solution of 0.0162 g of isomer B of α-(2-carbo-tert.butyloxy-3,3-dimethyl-7-oxo-4-thia-2,6-diaza-6-bicyclo[3,2,0]-heptyl)-α-(phenylacetylmethylene)-acetic acid tert.-butyl ester in 10.6 ml of benzene in a Pyrex glass vessel is irradiated with ultra-violet light at room temperature and under a nitrogen atmosphere. After 90 minutes the solvent is distilled off; according to a nuclear resonance spectrum the non-crystalline residue consists of an approximately 42:58-mixture of isomer A and isomer B of α-(2-carbo-tert.-butyloxy-3,3-dimethyl-7-oxo-4-thia-2,6-diaza-6-bicyclo[3,2,0]heptyl)-α-phenylacetylmethylene)-acetic acid tert.-butyl ester.

The crystalline isomer B and fractions which predominantly consist of isomer B of α-(2-carbo-tert.-butyloxy-3,3-dimethyl-7-oxo-4-thia-2,6-diaza-6-bicyclo[3,2,0]heptyl)-α-(phenylacetylmethylene)-acetic acid tert.-butyl ester can in the same manner be isomerised to give isomer mixtures containing isomer A and isomer B of α-(2-carbo-tert.-butyloxy-3,3-dimethyl-7-oxo-4-thia-2,6-diaza-6-bicyclo[3,2,0]heptyl)-α-phenylacetylmethylene)-acetic acid tert.-butyl ester.

EXAMPLE 24

1 g of α-(2-carbo-tert.-butyloxy-3,3-dimethyl-7-oxo-4thia-2,6-diaza-6-bicyclo[3,2,0]heptyl)-α-(triphenylphosphoranylidene)-acetic acid tert.-butyl ester is treated under nitrogen with 0.65 g of isopropylglyoxal (in enol form) in 7 ml of toluene and the mixture is allowed to stand for 8 days at 90°. The solvent and the excess isopropylglyoxal are removed at 50° under reduced pressure and the residue is chromatographed on 50 g of acid-washed silica gel; elution is carried out with a 4:1-mixture of hexane and ethyl acetate. The first 150 ml elute the isomer A (trans) of α-(2-carbo-tert.-butyloxy-3,3-dimethyl-7-oxo-4-thia-2,6-diaza-6-bicyclo[3,2,0]heptyl)-α-(isobutyryl-methylene)-acetic acid tert.-butyl ester of the formula

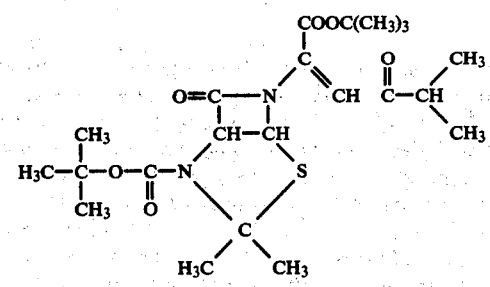

which after crystallisation from a mixture of hexane and ethyl acetate melts at 133°–134°; ultra-violet absorption spectrum:$\lambda_{max}$ 294 mμ (in ethanol); $\lambda_{max}$ 330 mμ (in potassium hydroxide/ethanol) and $\lambda_{max}$ 330 mμ (in hydrogen chloride/ethanol); infra-red absorption spectrum (in methylene chloride): characteristic bands at 5.62μ, 5.80μ (shoulder), 5.84–5.94μ and 6.26μ.

The isomer B (cis) of α-(2-carbo-tert.-butyloxy-3,3-dimethyl-7-oxo-4-thia-2,6-diaza-6-bicyclo[3,2,0]heptyl)-α-(isobutyrylmethylene)-acetic acid tert.-butyl ester is obtained on further elution with the same solvent mixture and melts at 146°–147° after crystallisation from a mixture of hexane and ethyl acetate; ultra-violet absorption spectrum:$\lambda_{max}$ 289 mμ (in ethanol); $\lambda_{max}$ 328 mμ (in potassium hydroxide/ethanol); and $\mu_{max}$ 328 mμ (in hydrogen chloride/ethanol); infra-red absorption spectrum (in methylene chloride): characteristic bands at 5.60–5.66μ5.75μ (shoulder), 5.85–5.95μ and 6.31μ.

EXAMPLE 25

A mixture of 0.05 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 0.0355 g of 4-nitrobenzyl-glyoxal in 0.6 ml of toluene is heated for 7 hours at 80°. The solvent is then distilled off under reduced pressure and the residue is chromatographed on a thin layer silica gel plate (20 × 20 × 0.15 cm), using a 2:1-mixture of hexane and ethyl acetate. Two yellow bands are obtained, with the upper band yielding the isomer A of α-(2-carbo-tert.-butyloxy-3,3-dimethyl-7-oxo-4-thia-2,6-diaza-6-bicyclo[3,2,0]heptyl)-α-[(4-nitro-phenylacetyl)-methylene]-acetic acid tert.-butyl ester of the formula

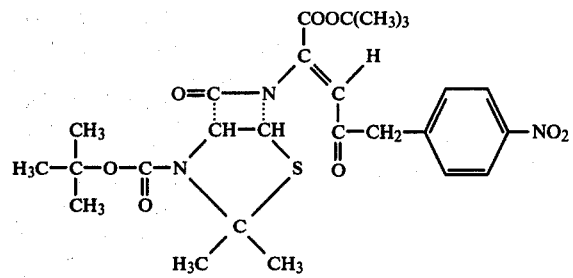

having an Rf-value = 0.41; ultra-violet absorption spectrum:$\lambda_{max}$ 288 mμ (broad; in ethanol) and $\lambda_{max}$ 505 mμ and 262 mμ (potassium hydroxide/ethanol); infra-red absorption spectrum (in methylene chloride): characteristic bands at 5.63μ, 5.83μ (shoulder), 5.88–5.92μ, 5.97μ (shoulder), 6.28–6.33μ, 6.59μ and 7.45μ; and the lower band yielding the isomer B of α-(2-carbo-tert.-butyloxy-3,3-dimethyl-7-oxo-4-thia-2,6-diaza-6-bicyclo[3,2,0]heptyl)-α-[4-nitro-phenylacetyl)-methylene]-acetic acid tert.-butyl ester of the formula

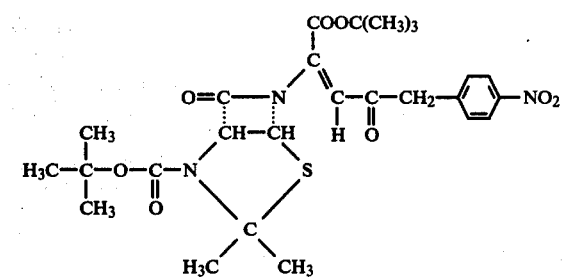

as yellow glass-like products. Isomer B crystallises from hexane, m.p. 173°; Rf-value: 0.29; ultra-violet absorption spectrum:$\lambda_{max}$ 293 mμ (in ethanol) and $\lambda_{max}$ 335 mμ and 285 mμ (in potassium hydroxide/ethanol); infra-red absorption spectrum (in methylene chloride): characteristic bands at 5.62μ, 5.77μ (shoulder), 5.83–5.92μ, 6.30–6.35μ, 6.59μ and 7.45μ.

The 4-nitrobenzylglyoxal used above as the starting material can be manufactured as follows: A solution of about 4 g of diazomethane in 200 ml of dry ether is mixed dropwise, while stirring, with 6 g of 4-nitrophenylacetyl chloride in 80 ml of dry tetrahydrofuran, with the temperature being kept at 0°–5° by stirring in a bath of ice-water. After about 30 minutes the addition is complete; the reaction mixture is stirred for a further 15 minutes at 0°–5° and is then evaporated in a rotational evaporator. The solid residue is dissolved in a mixture of methylene chloride and ether and the small amount of solid material is filtered off and the filtrate is evaporated. The 4-nitrobenzyl-diazomethylketone is thus obtained, which after crystallisation from a mixture of ether and hexane melts at 90°–92°; infra-red absorption spectrum (in methylene chloride): characteristic bands at 4.78μ, 6.10μ, 6.26μ, 6.58μ and 7.45μ.

A solution of 3 g of 4-nitrobenzyl-diazomethylketone in 100 ml of a 1:1-mixture of ether and methylene chloride is mixed with a solution of 4.22 g of triphenylphosphine in 100 ml of ether. After about 5 minutes the 1-(4-nitrophenyl)-3-(triphenylphosphoranylidenehydrazono)-acetone crystallises out at room temperature; the mixture is filtered and the mother liquor is concentrated to yield a further quantity of the crystalline product. The crude product is crystallised from a mixture of 50 ml of methylene chloride and 250 ml of hexane, m.p. 160°–165°; ultra-violet absorption spectrum (in ethanol):$\lambda_{max}$ 320 m$\mu$ and 270–275 m$\mu$ (shoulder); infra-red absorption spectrum (in methylene chloride): characteristic bands at 6.10$\mu$ (shoulder), 6.14–6.20$\mu$, 6.32$\mu$, 6.67–6.74$\mu$ and 7.45$\mu$.

A suspension of 0.467 g of 1-(4-nitrophenyl)-3-(triphenyl-phosphoranylidene-hydrazono)-acetone in 3 ml of tetrahydrofuran is mixed with 0.21 g of pulverized sodium nitrite and 1.2 ml of water. The mixture is cooled to 0°–5° and 2.2 ml of 2N hydrochloric acid are added dropwise over the course of 2 minutes, whereupon an emulsion forms. After 60 minutes at 0°–5°, the aqueous layer is separated and extracted four times with 10 ml of methylene chloride at a time. The combined organic solutions are twice washed with 10 ml of a saturated aqueous chloride solution each time and are evaporated; the residue is chromatographed on 20 g of acid-washed silica gel. The crystalline and enolised 4-nitrobenzylglyoxal, m.p. 163°–164°, is eluted with 600 ml of benzene; ultra-violet absorption spectrum:$\lambda_{max}$ 343 m$\mu$ (in ethanol); 444 m$\mu$ (in potassium hydroxide/ethanol) and $\lambda_{max}$ 343 m$\mu$ (in hydrogen chloride/ethanol); infra-red absorption spectrum (in methylene chloride): characteristic bands at 3.02$\mu$, 5.98$\mu$, 6.06$\mu$, 6.28$\mu$, 6.60$\mu$ and 7.47$\mu$; whereas the hydrate of 4-nitrobenzylglyoxal is eluted as a non-crystalline syrupy material with 350 ml of a 9:1-mixture of benzene and ethyl acetate; infra-red absorption spectrum (in methylene chloride): characteristic bands at 3.01$\mu$, 5.82$\mu$, 6.27$\mu$, 6.61$\mu$ and 7.47$\mu$.

EXAMPLE 26

A mixture of 0.872 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 0.611 g of 4-nitrobenzylglyoxal hydrate in 10.5 g of toluene is heated at 80° for 6½ hours. The solvent is distilled off under reduced pressure and the residue is chromatographed on 50 g of acid-washed silica gel. The isomer A of α-(2-carbo-tert.-butyloxy-3,3-dimethyl-7-oxo-4-thia-2,6-diaza-6-bicyclo[3,2,0]heptyl)-α-[(4-nitro-phenylacetyl)-methylene]-acetic acid tert.-butyl ester is eluted with 1300 ml of benzene and 500 ml of a 98.5:1.5-mixture of benzene and ethyl acetate, a mixture of the two isomers A and B of α-(2-carbo-tert.-butyloxy-3,3-dimethyl-7-oxo-4-thia-2,6-diaza-6-bicyclo[3,2,0]heptyl)-α-[(4-nitro-phenylacetyl)-methylene]-acetic acid tert.-butyl ester is eluted with 200 ml of a 96:4-mixture of benzene and ethyl acetate, and isomer B of α-(2-carbo-tert.-butyloxy-3,3-dimethyl-7-oxo-4-thia-2,6-diaza-6-bicyclo[3,2,0]heptyl)-α-[(4-nitro-phenylacetyl)-methylene]-acetic acid tert.-butyl ester together with a small quantity of isomer A is eluted with a further 400 ml of the 96:4-mixture of benzene and ethyl acetate. The mixture is separated by means of thin layer chromatography (4 silica gel plates: 20 × 20 × 0.15 cm) using a 2:1-mixture of hexane and ethyl acetate; one thus obtains a further quantity of isomer A; Rf = 0.41; and of isomer B; Rf = 0.29. The latter is combined with the almost pure isomer B from the chromatogram and crystallised from hexane, m.p. 173°.

EXAMPLE 27

A mixture of 0.714 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 0.67 g of 4-methoxybenzylglyoxal hydrate in 8.6 ml of toluene is heated at 80° for 3½ hours and is then evaporated under reduced pressure. The residue is chromatographed on 50 g of acid-washed silica gel. The excess 4-methoxybenzylglyoxal is eluted in an anhydrous form with 500 ml of benzene, while with 800 ml of a 99:1-mixture of benzene and ethyl acetate the almost pure isomer A of α-(2-carbo-tert.-butyloxy-3,3-dimethyl-7-oxo-4-thia-2,6-diaza-6-bicyclo[3,2,0]heptyl)-α-[(4-methoxy-phenylacetyl)-methylene]acetic acid tert.-butyl ester of the formula

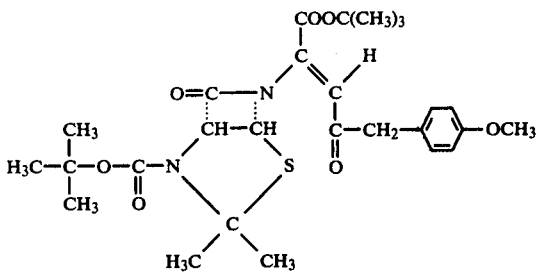

is eluted; m.p. 105°–107° after recrystallisation from a mixture of ethyl acetate and hexane; ultra-violet absorption spectrum:$\lambda_{max}$ 298 m$\mu$, 288 m$\mu$ (shoulder) and 225 m$\mu$ (shoulder) (in ethanol); $\mu_{max}$ 340 m$\mu$ (in potassium hydroxide/ethanol); infra-red absorption spectrum (in methylene chloride): characteristic bands at 5.63$\mu$, 5.82$\mu$ (shoulder), 5.87–5.97$\mu$, 6.23$\mu$ (shoulder), 6.28$\mu$, 6.63$\mu$ and 6.77$\mu$; with a further 400 ml of the 99:1-mixture of benzene and ethyl acetate, a mixture of the isomers A and B is eluted, and with 300 ml of a 98:2-mixture of benzene and ethyl acetate the isomer B of α-(2-carbo-tert.-butyloxy-3,3-dimethyl-7-oxo-4-thia-2,6-diaza-6-bicyclo[3,2,0]heptyl)-α-[(4-methoxy-phenylacetyl)-methylene]-acetic acid tert.-butyl ester of the formula

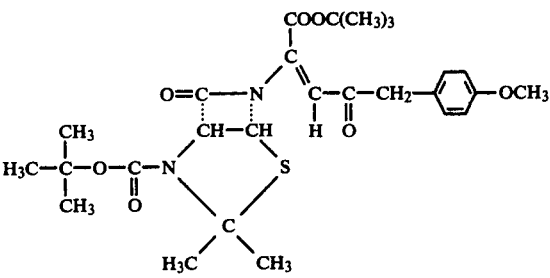

is eluted; the pure isomer B obtained from the mixed fraction by recrystallisation from hexane, and the pure isomer B obtained in the same manner from the isomer B fraction melt at 169°–170°; ultra-violet absorption spectrum:$\mu_{max}$ 289 m$\mu$ (broad) and 227 m$\mu$ (shoulder) (in ethanol); and $\mu_{max}$ 343 m$\mu$ (in potassium hydroxide/ethanol); infra-red absorption spectrum (in methylene chloride): characteristic bands at 5.59$\mu$, 5.75$\mu$ (shoulder), 5.80–5.93$\mu$, 6.24$\mu$ (shoulder), 6.30$\mu$ and 6.60$\mu$.

Further quantities of the two isomers A and B of α-(2-carbo-tert.-butyloxy-3,3-dimethyl-7-oxo-4-thia-2,6-diaza-6-bicyclo[3,2,0]heptyl)-α-[(4-methoxy-phenylacetyl)-methylene]-acetic acid tert.-butyl ester can be obtained from the combined mother liquors by means of preparative thin layer chromatography and development with a 2:1-mixture of hexane and ethyl acetate.

The 4-methoxybenzylglyoxal hydrate used as the starting material in the above example can be obtained as follows:

A solution of 7.43 g of 4-methoxy-phenylacetyl chloride in 100 ml of dry ether is added dropwise to a solution of 6 g of diazomethane in 300 ml of ether cooled to 0°–5°. The reaction mixture is stirred for a further 30 minutes, finally without cooling. The excess diazomethane and the solvent are removed under reduced pressure in a rotational evaporator, the residue is dissolved in 100 ml of ether, and the small amount of wax-like material is filtered off. After evaporation of the filtrate, the 4-methoxybenzyl-diazomethyl ketone is obtained; infra-red absorption spectrum (in methylene chloride): characteristic bands at 4.79$\mu$, 6.10$\mu$, 6.22$\mu$ (shoulder), 6.62$\mu$ and 7.73–7.45$\mu$; this material is further processed without purification.

A solution of 7.52 g of 4-methoxybenzyl-diazomethylketone in 300 ml of ether is mixed with 11.1 g of triphenylphosphine in 200 ml of ether. The reaction mixture is stirred at room temperature, whereupon a crystalline precipitate forms after a few minutes; this is filtered off after one hour and washed with cold ether. The 1-(4-methoxyphenyl)-3-(triphenylphosphoranylidene-hydrazono)-acetone, m.p. 111°–112°, is thus obtained; infra-red absorption spectrum (in methylene chloride): characteristic bands at 4.80$\mu$, 6.05$\mu$ (shoulder), 6.14$\mu$, 6.24$\mu$ (shoulder), and 6.63–6.70$\mu$; this is processed without further purification.

A solution of 1.82 g of 1-(4-methoxyphenyl)-3-(triphenylphosphoranylidene-hydrazono)-acetone in 12 ml of tetrahydrofuran is mixed with 0.84 g of pulverized sodium nitrite and the mixture is diluted with 5 ml of water. The resulting suspension is cooled to 0°–5°, treated dropwise over the course of 7 minutes with 8.8 ml of 2N hydrochloric acid and then kept for a further 30 minutes at 0°–5°. The aqueous phase is twice washed with methylene chloride; the combined organic solutions are washed with a saturated aqueous sodium chloride solution, dried over sodium sulphate and evaporated under reduced pressure. The oily residue is chromatographed on 40 g of acid-washed silica gel. A small quantity of a by-product is eluted with benzene and, using 1200 ml of a 95:5-mixture of benzene and ethyl acetate, the 4-methoxybenzylglyoxal is obtained in the form of the hydrate, which is an oily product; infra-red absorption spectrum (in methylene chloride): characteristic bands at 2.96$\mu$, 5.79–5.84$\mu$, 6.23$\mu$ and 6.63$\mu$. The anhydrous product melts at 139°–140° after recrystallisation from a mixture of chloroform and hexane; ultraviolet absorption spectrum:$\lambda_{max}$ 333 m$\mu$ (in ethanol or hydrochloric acid/ethanol) and $\lambda_{max}$ 367 m$\mu$ (in potassium hydroxide/ethanol); infra-red absorption spectrum (in methylene chloride): characteristic bands at 3.00$\mu$, 5.97$\mu$, 6.09$\mu$, 6.24$\mu$, 6.61$\mu$ and 7.15$\mu$.

EXAMPLE 28

A solution of 0.8 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 1.2 g of crude 4-chlorobenzyl-glyoxal hydrate in 12 ml of toluene is heated at 80° for 5 hours. The solvent is distilled off under reduced pressure, and the syrupy residue is dissolved in about 4 ml of benzene. The resulting crystalline precipitate, consisting of the enol of 4-chlorobenzyl-glyoxal, is filtered off and the filtrate is chromatographed on a column of 50 g of acid-washed silica gel. A further quantity of 4-chlorobenzyl-glyoxal is eluted with 500 ml of benzene, and a mixture of the isomers of α-(2-carbo-tert.-butyloxy-3,3-dimethyl-7-oxo-4-thia-2,6-diaza-6-bicyclo[3,2,0]heptyl)-α-[(4-chlorophenylacetyl)-methylene]-acetic acid tert.-butyl ester eluted with 200 ml of benzene and 800 ml of a mixture of benzene and ethyl acetate (97:3); the reaction mixture is chromatographed on a further 50 g of acid-washed silica gel by means of benzene and benzene containing 5% of ethyl acetate, and then separated by preparative thin-layer chromatography (system hexane:ethyl acetate 2:1). There is obtained the non-crystalline isomer A (trans) of α-(2-carbo-tert.-butyloxy-3,3-dimethyl-7-oxo-4-thia-2,6-diaza-6-bicyclo[3,2,0]heptyl)-α-[(4-chlorophenylacetyl)-methylene]-acetic acid tert.-butyl ester of the formula

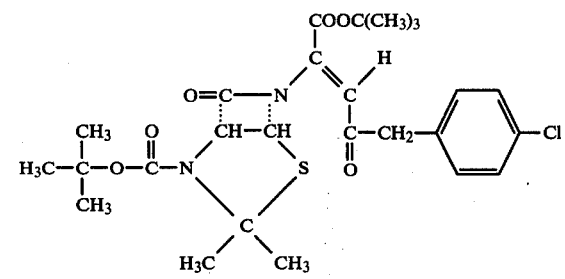

which shows the following bands in the ultraviolet absorption spectrum: $\lambda_{max}$ 300 m$\mu$ (in ethanol); $\lambda_{max}$ 342 m$\mu$ (in potassium hydroxide/ethanol); and $\lambda_{max}$ 338 m$\mu$ (on the addition of hydrogen chloride to the preceding sample); infra-red absorption spectrum (in methylene chloride): characteristic bands at 5.60$\mu$, 5.75$\mu$ (shoulder), 5.80–5.92$\mu$ (broad), 6.26$\mu$ and 6.70$\mu$; and the crystalline isomer B (cis) of α-(2-carbo-tert.-butyloxy-3,3-dimethyl-7-oxo-4-thia-2,6-diaza-6-bicyclo[3,2,0]heptyl)-α-[(4-chlorophenyl-acetyl)-methylene]-acetic acid tert.-butyl ester of the formula

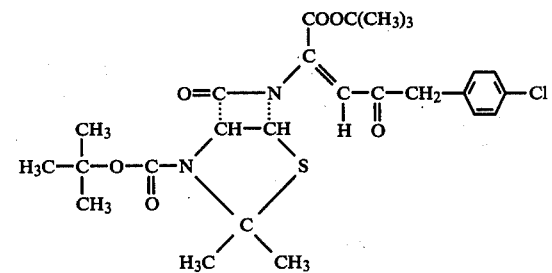

which, after recrystallisation from hexane, melts at 178°–179°; ultra-violet absorption spectrum:$\lambda_{max}$ 295 m$\mu$ (in ethanol); $\lambda_{max}$ 337 m$\mu$ (in potassium hydroxide/ethanol); and $\lambda_{max}$ 337 m$\mu$ (on the addition of hydrogen chloride to the preceding sample; infra-red absorption spectrum (in methylene chloride): characteristic bands at 5.59$\mu$, 5.75$\mu$ (shoulder), 5.78–5.94$\mu$; 6.07$\mu$ (shoulder), 6.31$\mu$ and 6.70$\mu$. The isomer A is processed without further purification.

The 4-Chlorobenzyl-glyoxal hydrate may be prepared as follows:

A solution of 16.5 g of 4-chloro-phenylacetyl chloride in 150 ml of dry ether is added dropwise, with vigorous stirring and cooling in an ice-water bath, to about 11 g of diazo-methane in 500 ml of ether. After being allowed to react for 30 minutes at 5°–10°, the diazomethane and the solvent are distilled off under reduced pressure. The 4-chlorobenzyl diazomethyl ketone obtainable as a yellowish crystalline residue; infrared absorption spectrum in methylene chloride: characteristic bands at 4.84μ, 6.22μ, 6.80μ and 7.47μ; is processed without any further purification.

A solution of 17 g of 4-chlorobenzyl diazomethyl ketone in 150 ml of ether is added at room temperature to a solution of 23.5 g of triphenyl phosphine in 300 ml of ether. The yellowish crystalline precipitate is filtered off after 20 minutes, washed with ether and recrystallised from a mixture of methylene chloride and ether; the resulting 1-(4-chlorophenyl)-3-(triphenylphosphoranylidene-hydrazono)-acetone melts at 130°–131°; ultra-violet absorption spectrum:λ$_{max}$ 320 mμ (ethanol); λ$_{max}$ 320 mμ (potassium hydroxide ethanol); and λ$_{max}$ 255–278 mμ (broad shoulder) (in hydrogen chloride/ethanol); infra-red absorption spectrum (in methylene chloride): characteristic bands at 4.76μ, 6.03μ (shoulder), 6.12μ, 6.28μ (shoulder) and 6.65–6.75μ.

A suspension of 8 g of 1-(4-chlorophenyl)-3-(triphenylphosphoranylidene-hydrazono)-acetone and 3.6 g of sodium nitrite in 51 ml of tetrahydrofuran and 22 ml of water is treated dropwise in the course of about 10 minutes with 37 ml of 2N hydrochloric acid while stirring and cooling in an ice-water bath (10°–13°), two phases being formed. Stirring is continued for 30 minutes at room temperature, the organic layer is separated, and the aqueous phase is extracted several times with methylene chloride. The combined organic solutions are dried over sodium sulphate and evaporated under reduced pressure. A syrupy residue is obtained which is chromatographed on 60 g of acid-washed silica gel. The crude 4-chlorobenzylglyoxal hydrate is extracted with benzene and a 95:5-mixture of benzene and ethyl acetate; ultra-violet absorption spectrum: λ$_{max}$ 222 mμ (in ethanol); λ$_{max}$ 365 mμ (in potassium hydroxide/ethanol); and λ$_{max}$ 316 mμ (in hydrogen chloride/ethanol); infra-red absorption spectrum (in methylene chloride): characteristic bands at 2.87–4.3μ, 5.77μ, 6.27μ and 6.72μ; the product is processed without any further purification. The anhydrous 4-chlorobenzylglyoxal in the enol form melts after recrystallisation from methylene chloride at 144°–147°; ultraviolet absorption spectrum:λ$_{max}$ 316 mμ (in ethanol); λ$_{max}$ 364 mμ (in potassium hydroxide+ethanol); and λ$_{max}$ 316 mμ (in hydrogen chloride+ethanol); infra-red absorption spectrum (in methylene chloride): characteristic bands at 2.92μ, 5.97μ, 6.07μ, 6.29μ and 6.71μ.

EXAMPLE 29

A solution of 2.5 g of α-(2-carbo-tert.-butyloxy-3,3-dimethyl-7-oxo-4-thia-2,6-diaza-6-bicyclo[3,2,0]heptyl)-α-(triphenylphosphoranylidene)-acetic acid tert.-butyl ester and 1.3 g of cyclohexylmethyl-glyoxal hydrate in 50 ml of toluene is heated for 4 hours at 80° and the solvent is evaporated under reduced pressure. The syrupy residue is triturated with ether, the resulting triphenyl phosphinoxide is filtered off and the filtrate is evaporated. The residue is chromatographed on 120 g of acid-washed silica gel and eluted with a 98:2- and a 9:1-mixture of hexane and ethyl acetate, to yield first the isomer A (trans) of α-(2-carbo-tert.-butyloxy-3,3-dimethyl-7-oxo-4-thia-2,6-diaza-6-bicyclo[3,2,0]heptyl)-α-(cyclohexyl-acetyl-methylene)-acetic acid tert.-butyl ester of the formula

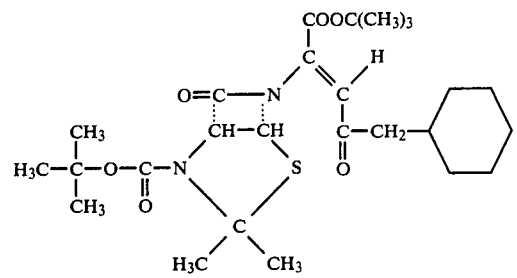

which is purified by means of preparative thin-layer chromatography (plates 20 × 20 × 0.15 cm; silica gel; system benzene:acetone 98:2) and is obtained in a syrupy form; optical rotation [α]$_D^{20}$ = −451° ± 1° (c = 0.87 in chloroform); ultraviolet absorption spectrum:-λ$_{max}$ 297 mμ (in ethanol); λ$_{max}$ 334 mμ (in potassium hydroxide/ethanol); and λ$_{max}$ 334 mμ (on the addition of hydrogen chloride to the alkaline sample); infra-red absorption spectrum (in methylene chloride); characteristic bands at 3.45μ, 3.50μ, 5.16μ, 5.78μ (shoulder), 5.80μ-5.95μ, 6.07μ (shoulder) and 6.28μ.

The isomer B (cis) of α-(2-carbo-tert.-butyloxy-3,3-dimethyl-7-oxo-4-thia-2,6-diaza-6-bicyclo[3,2,0]heptyl)-α-(cyclohexylacetyl-methylene)-acetic acid tert.-butyl ester of the formula

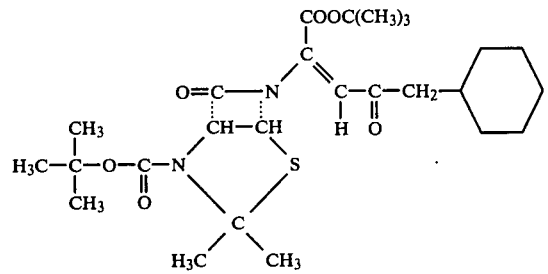

is eluted as second product and crystallised from hexane; m.p. 154°–155°; optical rotation [α]$_D$ = −232° ± 1° (c = 0.8 in chloroform); ultra-violet absorption spectrum: λ$_{max}$ 288 mμ (in ethanol), λ$_{max}$ 333 mμ (in potassium hydroxide/ethanol) and λ$_{max}$ 333 mμ (on addition of hydrogen chloride to the above alkaline sample); infra-red absorption spectrum (in methylene chloride): characteristic bands at 3.44μ, 3.53μ, 5.60μ, 5.75μ (shoulder), 5.80–5.93μ, 6.05μ (shoulder) and 6.31μ.

The cyclohexalmethylglyoxal hydrate used as starting material may be prepared as follows:

A solution of 19.8 g of cyclohexylacetyl chloride (b.p. 98°–100°/23 mm Hg) in 150 ml of dry ether is slowly added at 0°–5° with cooling in an ice-water bath to a vigorously stirred solution of 11 g of diazomethane in 500 ml of ether. The excess diazomethane and ether is distilled off under reduced pressure and cyclohexylmethyl diazomethyl ketone is obtained as residue; infra-red absorption spectrum (in methylene chloride): characteristic bands at 3.45μ, 3.52μ, 4.75μ and 6.12μ; the product is processed without any further purification. A solution of 20 g of cyclohexalmethyl diazomethyl ketone in 100 ml of ether is added in one portion, with stirring, to a solution of 32 g of triphenylphosphine in 450 ml of ether. After stirring for 30 minutes at room temperature, the solvent is evaporated under reduced pressure. The 1-cyclohexyl-3-(triphenylphosphoranylidene-hydrazono)-acetone obtainable as oily residue crystallises in the cold from ether; m.p. 58°–62°; ultraviolet absorption spectrum: $\lambda_{max}$ 314 mμ, 262–275 mμ and 223 mμ (in ethanol and in potassium hydroxide/ethanol), and $\lambda_{max}$ 257–275 mμ and 230 mμ (in hydrogen chloride/ethanol); infra-red absorption spectrum (in methylene chloride): characteristic bands at 3.43μ, 3.56μ, 4.76μ, 6.15μ and 6.67μ.

77 ml of 2N hydrochloric acid are added slowly, with stirring and cooling to 10°–13° (ice-water bath), to a mixture of 15 g of 1-cyclohexyl-3-(triphenylphosphoranylidene-hydrazono-acetone and 7.37 g of sodium nitrite in 120 ml of tetrahydrofuran and 42 ml of water. After another 30 minutes at room temperature the organic solution is separated and the aqueous phase is extracted with methylene chloride. The combined organic solutions are dried over sodium sulphate and evaporated under reduced pressure. The syrupy residue is treated with ether, the resulting triphenyl phosphinoxide is filtered off and the filtrate is evaporated. The residue is chromatographed on a column of 120 g of acid-washed silica gel, elution being carried out with about 3000 ml of a 97:3-mixture of hexane and ethyl acetate to yield the cyclohexylmethyl-glyoxal hydrate as a syrupy product; infra-red absorption spectrum (in methylene chloride): characteristic bands at 2.90–4.1μ (broad); 3.47μ, 3.53μ and 5.80μ; the product is further processed without purification.

EXAMPLE 30

A solution of 2.55 g of the mixture of the isomers of α-(2-carbo-tert.-butyloxy-3,3-dimethyl-7-oxo-4-thia-2,6-diaza-6-bicyclo[3,2,0]heptyl)-α-(carboxymethylene)-acetic acid tert.-butyl ester in 80 ml of a 9:1-mixture of acetic acid and water is mixed every 15 minutes with 0.5 g of zinc dust at room temperature, and with vigorous stirring, until the reduction is complete. After one hour, only a small quantity of starting material can still be detected; the addition of zinc dust is interrupted and the mixture is stirred for a further 2 hours at room temperature and then mixed with 60 ml of water and 60 ml of methylene chloride. It is filtered through cottonwool and then extracted four times with 100 ml of methylene chloride at a time. The combined methylene chloride solutions are dried over sodium sulphate and evaporated at 45° under reduced pressure. The residue is repeatedly mixed with benzene and the latter is evaporated each time until the acetic acid is completely removed. The crude residue is filtered through acid-washed silica gel (diameter: 4 cm; hight: 10 cm), elution being carried out with a 2:1-mixture of hexane and ethyl acetate; the mixture of the isomers of α-(2-carbo-tert.-butyloxy-3,3-diemthyl-7-oxo-4-thia-2,6-diaza-6-bicyclo[3,2,0]heptyl)-α-(carboxymethyl)-acetic acid tert.-butyl ester of the formula

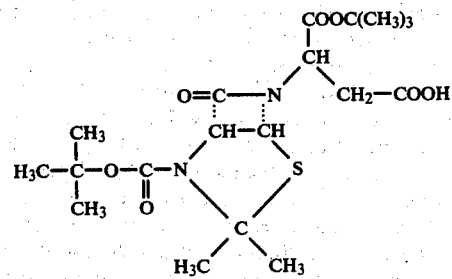

is thus obtained; this can be separated almost completely by crystallisation from ether and hexane. The isomer A is first obtained, and melts in a somewhat impure form, after recrystallisation from an ether-hexane mixture, at 169°–171°; analytical sample: m.p. 172°–173°; $[α]_D^{20} = -295° \pm 1°$ (c =1.168 in chloroform); thin layer chromatograhy (silica gel; system toluene:acetic acid:water 5:4:1): Rf = 0.35; infra-red absorption spectrum (in methylene chloride): characteristic bands at 5.68μ, 5.72μ and 5.90μ.

The first mother liquor predominantly contains isomer B which can be purified as follows: A solution of 0.1983 g of the mother liquor residue containing isomer B in 5 ml of methylene chloride is mixed with 2.26 ml of a solution of 1.9836 g of cyclohexylamine in 100 ml of ether and the solution is evaporated. The residue is taken up in methylene chloride and filtered, the filtrate is evaporated and the residue is crystallised from a mixture of methylene chloride and acetone. The crystalline material obtainable in this way and that from the working-up of the mother liquor are dissolved in 5 ml of methylene chloride, shaken with 5 ml of water containing 0.5 ml of 2N sulphuric acid and the aqueous phase is back-washed with 10 ml of methylene chloride. The organic solutions are washed with 10 ml of water, dried over sodium sulphate and evaporated; the pure isomer B of α-(2-carbo-tert.-butyloxy-3,3-dimethyl-7-oxo-4-thia-2,6-diaza-6-bicyclo[3,2,0]heptyl)-α-(carboxymethyl)-acetic acid tert.-butyl ester is thus obtained, m.p. 116°–117°; $[α]_D^{20} = -252° \pm 1°$ (c = 0.924 in chloroform); thin layer chromatography (silica gel; system toluene:acetic acid:water 5:4:1): Rf = 0.33; infra-red absorption spectrum (in methylene chloride): characteristic bands at 5.68μ, 5.78μ and 5.85–5.90μ.

EXAMPLE 31

A solution of 0.065 g of the isomer mixture of α-(2-carbo-tert.-butyloxy-3,3-dimethyl-7-oxo-4-thia-2,6-diaza-6-bicyclo[3,2,0]heptyl)-α-(carbethoxymethylene)-acetic acid 2,2,2-trichloroethyl ester in 2 ml of a 4:1-mixture of hexane and methylene chloride is mixed at room temperature, in a carbon monoxide-nitrogen atmosphere, with about 2 mol equivalents of cobalt hydrocarbonyl in hexane over the course of one hour. The reducing reagent is manufactured as follows: A solution of 0.39 g of dicobaltoctacarbonyl in 10 ml of dry hexane is mixed with 3 ml of dimethylformamide under a nitrogen atmosphere and is stirred for half an hour. A two-phase system is obtained; the upper layer is colourless and the lower layer is red. 8 ml of a 1:1-mixture of concentrated hydrochloric acid and 2N hydrochloric acid are then added while cooling in an ice bath and the mixture is stirred for one hour at 0°. The blue acid layer is separated and the yellow hexane solution is washed three times with 1 ml of water. The hexane solution contains 1.47 mmols of cobalt hydrocarbonyl of the formula H-Co(CO)$_4$ and is used in this form.

The reaction mixture is then filtered through a column (hight: 7 cm; diameter: 2 cm) of silica gel and is eluted with benzene (cobalt derivative) and with 20 ml of a 3:1-mixture of benzene and ethyl acetate. From the latter mixture a crude product is obtained which is again chromatographed on silica gel and eluted with 49:1-, 19:1- and 4:1-mixtures of benzene and ethyl acetate. The isomer A of α-(2-carbo-tert.-butyloxy-3,3-dimethyl-7-oxo-4-thia-2,6-diaza-6-bicyclo[3,2,0]heptyl)-α-(carbethoxymethyl)-acetic acid 2,2,2-trichloroethyl ester of the formula

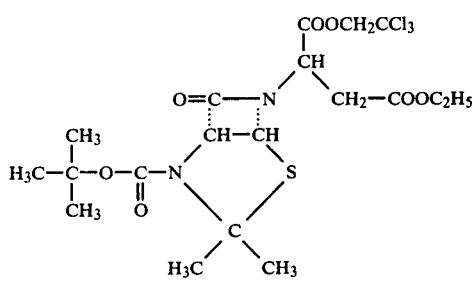

m.p. 90° after crystallisation from pentane, and a mixture of isomer B with small amount of isomer A, as well as a small quantity of 2-carbo-tert.-butyloxy-3,3-dimethyl-4-thia-2,6-diaza-bicyclo[3,2,0]heptan-7-one are obtained.

EXAMPLE 32

A hexane solution of 1.47 mmols of cobalt hydrocarbonyl is mixed with 0.2 g of α-(2-carbo-tert.-butyloxy-3,3-dimethyl-7-oxo-4-thia-2,6-diaza-6-bicyclo[3,2,0]heptyl)-α-(carbo-tert.-butyloxy-methylene)-acetic acid 2,2,2-trichloroethyl ester in 2 ml of a 4:1 mixture of hexane and methylene chloride; the reaction mixture turns dark brown. After standing for 30 minutes at room temperature, it is filtered through silica gel. The cobalt compounds are eluted with benzene until the silica gel is colourless and elution is then carried out with a 9:1-mixture of benzene and ethyl acetate, whereby a mixture of the isomers of α-(2-carbo-tert.-butyloxy-3,3-dimethyl-7-oxo-4-thia-2,6-diaza-6-bicyclo[3,2,0]heptyl)-α-(carbo-tert.-butyloxymethyl)-acetic acid 2,2,2-trichloroethyl ester of the formula

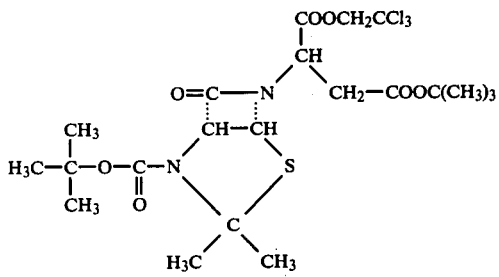

is obtained, while 2-carbo-tert.-butyloxy-3,3-dimethyl-4-thia-2,6-diaza-bicyclo[3,2,0]heptan-7-one is eluted with a 3:1-mixture of benzene and ethyl acetate. After crystallisation from a mixture of methylene chloride and pentane, the mixture of the two isomers melts at 95°–105°, and after a further crystallisation the isomer A, m.p. 108°, is obtained; $[\alpha]_D^{20} = -240° \pm 1°$ (c = 0.452 in chloroform); ultra-violet absorption spectrum (in ethanol): $\lambda_{max} = 230$ mμ (weak); infra-red absorption spectrum (in methylene chloride); characteristic bands at 5.65μ, 570μ, 5.85μ and 5.90μ.

EXAMPLE 33

A mixture of 0.0414 g of α-(2-carbo-tert.-butyloxy-3,3-dimethyl-7-oxo-4-thia-2,6-diaza-6-bicyclo[3,2,0]heptyl)-α-(carbo-tert.-butyloxy-methylene)-acetic acid 2,2,2-trichloroethyl ester in 4 ml of ethyl acetate is hydrogenated for 45 minutes under atmospheric pressure at 30° in the presence of 0.0524 g of a 10% palladium-on-charcoal catalyst. After filtration, the filtrate is evaporated and the residue is purified by filtration through 1.2 g of acid-washed silica gel. A polar material is eluted with 15 ml of benzene and the bulk of the isomer mixture of α-(2-carbo-tert.-butyloxy-3,3dimethyl-7-oxo-4-thia-2,6-diaza-6-bicyclo[3,2,0]heptyl)-α-(carbo-tert.-butyloxy-methyl)-acetic acid 2,2,2,-trichloroethyl ester with 5 ml of a 9:1-mixture of benzene and ethyl acetate; after crystllisation from pentane, it melts at 90°–96°.

EXAMPLE 34

A solution of 1.98 g of dicobalt octacarbonyl in 25 ml of hexane is mixed with 6 ml of dimethylformamide while stirring in a nitrogen atmosphere. After 30 minutes, two phases, an upper yellow phase and a lower red phase, are formed. The mixture is cooled to 0°, mixed with 10 ml of a 1:1-mixture of 2N hydrochloric acid and concentrated hydrochloric acid while stirring, and kept for one hour at about 0°. The blue acid layer is separated and the remaining mixture is washed three times with 5 ml of water and then dried with a small amount of sodium sulphate.

A solution of 1.039 g of α-(2-carbo-tert.-butyloxy-3,3-dimethyl-7-oxo-4-thia-2,6-diaza-6-bicyclo[3,2,0]heptyl)-α-(carbo-tert.-butyloxy-methylene)-acetic acid 2,2,2-trichloroethyl ester in 3 ml of methylene chloride and 4 ml of n-hexane is mixed, in a nitrogen atmosphere, with the cobalt hydrocarbonyl solution prepared according to the above process, and the mixture is stirred for 15 minutes at room temperature and is then filtered through acid-washed silica gel. The column (diameter: 2 cm; hight: 25 cm) is washed with benzene until colourless and the mixture of isomers of α-(2-carbo-tert.-butyloxy-3,3-dimethyl-7-oxo-4-thia-2,6-diaza-6-bicyclo[3,2,0]heptyl)-α-(carbo-tert.-butyloxymethyl)-acetic acid 2,2,2-trichloroethyl ester is then eluted with a 19:1 mixture of benzene and ethyl acetate. Isomer A, m.p. 108°–110°, is obtained by repeated crystallisation from pentane; the mother liquor mainly contains a 1:1-mixture of the two isomers. The isomer A has the following configuration

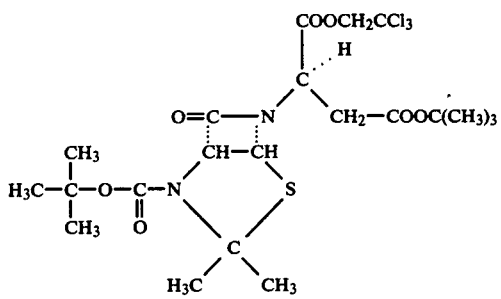

EXAMPLE 35

A solution of 0.205 g of α-(2-carbo-tert.-butyloxy-3,3-dimethyl-7-oxo-4-thia-2,6-diaza-6-bicyclo[3,2,0]-heptyl)-α-(carbo-tert.-butyloxymethylene)-acetic acid 2,2,2-trichloroethyl ester (mixture of both isomers) in 6 ml of a 4:1-mixture of hexane and methylene chloride is mixed, at room temperature and under a nitrogen atmosphere, with 3 equivalents of cobalt hydrocarbonyl in 10 ml of hexane and the mixture is then filtered through a column of silica gel (2 cm of diameter and 8 cm length), with the cobalt compounds being eluted with benzene and the reduction products being eluted with a 3:1-mixture of benzene and ethyl acetate. The crude product is again filtered through silica gel (column diameter: 1 cm; hight: 25 cm), with a forerun being eluted with 100 ml of benzene, and isomer of the starting material being eluted with 150 ml of a 99:1 mixture of benzene and ethyl acetate, the isomer B of α-(2-carbo-tert.-butyloxy-3,3-dimethyl-7-oxo-4-thia-2,6-diaza-6-bicyclo[3,2,0]-α-(carbo-tert.-butyloxymethyl)-acetic acid 2,2,2-trichloroethyl ester, followed by a mixture of the two isomers and the pure isomer B being eluted with 200 ml of 49:1-mixture of benzene and ethyl acetate, and a small quantity of 2-carbo-tert.-butyloxy-3,3-dimethyl-4-thia-2,6-diaza-bicyclo[3,2,0]heptan-7-one then being eluted with 80 ml of a 4:1-mixture of benzene and ethyl acetate. The isomer B has the following configuration

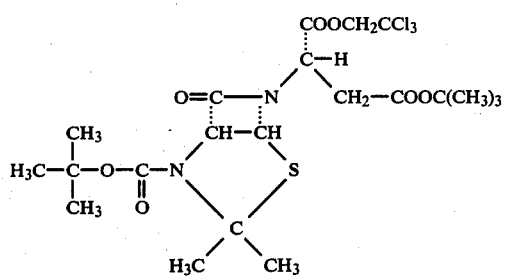

and melts at 92°–93° after crystallisation from pentane; $[\alpha]_D^{20} = -197° \pm 1°$ (c = 0.555 in chloroform); ultra-violet absorption spectrum (in ethanol); weak absorption at 230–240 mμ; infra-red absorption spectrum (in methylene chloride); characteristic bands at 5.65μ, 5.725μ and 5.85–5.95μ.

EXAMPLE 36

A mixture of 0.035 g of isomer A of α-(2-carbo-tert.-butyloxy-3,3-dimethyl-7-oxo-4-thia-2,6-diaza-6-bicyclo[3,2,0]-heptyl)-α-(carbo-tert.-butyloxymethyl)-acetic acid 2,2,2-trichloroethyl ester (Example 34) and 2 ml of pre-cooled trifluoroacetic acid is allowed to stand for 25 minutes at 0° and is then evaporated in a high vacuum and mixed with 3 ml of a saturated aqueous solution of sodium acetate. The reaction mixture is extracted with methylene chloride and the organic solution is dried over sodium sulphate and evaporated. The residue crystallises from a mixture of ether and pentane and yields the α-(3,3-dimethyl-7-oxo-4-thia-2,6-diaza-6-bicyclo[3,2,0]heptyl)-α-(carbo-tert.-butyloxy-methyl)acetic acid 2,2,2-trichloroethyl ester of formula

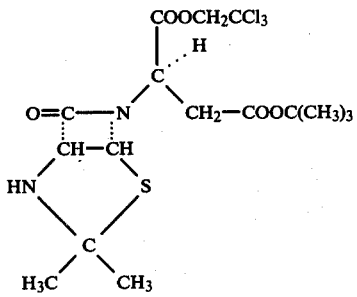

which melts at 136°–138°; $[\alpha]_D^{20} = -112° \pm 2°$ (c = 0.625 in chloroform); thin layer chromatography (silica gel): Rf = 0.25 in a 3:1-mixture of benzene and ethyl acetate; infra-red absorption spectrum (in methylene chloride): characteristic bands at 2.12μ, 5.74μ, 5.84μ and 7.34μ.

EXAMPLE 37

A mixture of 0.75 g of the isomer mixture of α-(2-carbo-tert.-butyloxy-3,3-dimethyl-7-oxo-4-thia-2,6-diaza-6-bicyclo[3,2,0]heptyl)-α-(carboxymethylene)-acetic acid tert.-butyl ester in 20 ml of a 9:1-mixture of acetic acid and water is treated over the course of 3½ hours with small quantities of a total of 4 g of zinc at room temperature and is then mixed with 20 ml of water, and the mixture is filtered through cottonwool. Extraction is carried out three times with 30 ml of methylene chloride each time. The organic extracts are dried over sodium sulphate and evaporated, acetic acid residues being removed azeotropically together with the benzene under reduced pressure; the latter operation is repeated 5 times. The residue is filtered through a silica gel column (1.8 cm diameter; 5.5 cm hight), elution being carried out with a 1:1-mixture of hexane and ethyl acetate and finally with ethyl acetate. A 1:1-mixture of the isomers of α-(2-carbo-tert.-butyloxy-3,3-dimethyl-7-oxo-4-thia-2,6-diaza-6-bicyclo[3,2,0]heptyl)-α-(carboxymethyl)-acetic acid tert.-butyl ester is thus obtained. Crystallisation from a mixture of ether and hexane at room temperature yields isomer A, which after recrystallisation from hexane at 0°, melts at 169°–173° (analytical sample: 172°–173°); $[\alpha]_D^{20} = -295° \pm 1°$ (c = 1.168 in chloroform); thin layer chromatogram (silica gel): Rf = 0.35 in a 5:4:1-mixture of toluene, acetic acid and water; infra-red absorption spectrum (in methylene chloride): characteristic bands at 5.68μ, 5.72μ and 5.90μ.

The mother liquor from the above crystallisation of the isomer mixture is concentrated and allowed to stand for 16 hours at room temperature, whereupon a further quantity of the isomer A is obtained. The filtrate is evaporated and recrystallised from hexane (0°; 7 days); isomer B is thus obtaineed, m.p. 116°–117°; $[\alpha]_D^{20} = -252° \pm 1°$ (c = 0.924 in chloroform); thin layer chromatogram (silica gel); Rf = 0.35–0.33 in a 5:4:1-mixture of toluene, acetic acid and water; infra-red absorption spectrum (in methylene chloride): characteristic bands at 5.68μ, 5.78μ and 5.85–5.90μ.

The resolution of 0.583 g of the mixture of isomers of α-(2-carbo-tert.-butyloxy-3,3-dimethyl-7-oxo-4-thia-2,6-diaza-6-bicyclo[3,2,0]heptyl)-α-(carboxymethyl)-acetic acid tert.-butyl ester can also be carried out chromatographically on acid-washed silica gel (column: 3 cm diameter; and 35 cm hight), with 300 ml of a 49:1-mixture, 300 of a 19:1-mixture, 450 ml of a 9:1-mixture, 300 ml of a 4:1-mixture, 300 ml of a 3:1-mixture, 300 ml of a 2:1-mixture and 300 ml of a 1:1-mixture of hexane and ethyl acetate and 400 ml of ethyl acetate being used as elution liquids. Isomer A is eluted with the 3:1- and the 2:1-mixture before isomer B and melts at 172°–173° after crystallisation from hexane.

An almost complete separation of the two isomers A and B of α-(2-carbo-tert.-butyloxy-3,3-dimethyl-7-oxo-4-thia-2,6-diaza-6-bicyclo[3,2,0]heptyl)-α-(carboxymethyl)-acetic acid tert.-butyl ester can, for example, also be carried out by mixing 0.1 g of the 1:1-isomer mixture in 3 ml of methylene chloride with 1.16 ml of a 100 ml solution of 1.9836 g of cyclohexylamine in ether (1 equivalent). The main portion of the isomer A precipitates as a gel and is shaken with 2 ml of methylene chloride and 1.2 ml of water containing 0.12 ml of 2N aqueous sulphuric acid. The organic phase is washed with 2.5 ml of water and the aqueous phase with 2.5 ml of methylene chloride; the organic extracts are combined, dried over sodium sulphate and evaporated; a 7:1-mixture of the isomers A and B is thus obtained.

EXAMPLE 38

A mixture of 0.027 g of the isomer A of α-(2-carbo-tert.-butyloxy-3,3-dimethyl-7-oxo-4-thia-2,6-diaza-6-bicyclo [3,2,0]heptyl)-α-(carboxymethyl)-acetic acid tert.-butyl ester and 1 ml of pre-cooled trifluoroacetic acid is kept for 30 minutes at −10° and is then evaporated at −10° under a high vacuum and mixed with 10 ml of ether. The solution is washed once with 4 ml and once with 1 ml of a saturated aqueous sodium hydrogen carbonate solution and is then mixed with 4 ml of a saturated phosphate buffer solution (pH 6) and adjusted to pH 5–6 with 3.75 ml of 2N aqueous sulphuric acid. The mixture is extracted twice with 10 ml of ether each time and the organic phase is once washed with 2 ml of water, dried over sodium sulphate and evaporated. The non-crystalline isomer A of α-(3,3-dimethyl-7-oxo-4-thia-2,6-diaza-6-bicyclo[3,2,0]heptyl)-α-(carboxymethyl)-acetic acid tert.-butyl ester of the formula

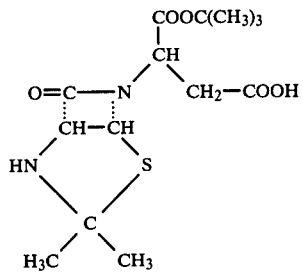

is thus obtained and has an Rf = 0.31 in a thin layer chromatogram (silica gel) in a 5:5:1-mixture of toluene, acetic acid and water.

EXAMPLE 39

A mixture of 0.105 g of the isomer B of α-(2-carbo-tert.-butyloxy-3,3-dimethyl-7-oxo-4-thia-2,6-diaza-6-bicyclo[3,2,0]heptyl)-α-(carboxymethyl)-acetic acid tert.-butyl ester and 2.5 ml of trifluoroacetic acid pre-cooled to −8° is kept for 35 minutes at −10° and is then evaporated under a high vacuum. The crude product is mixed with 40 ml of a 1:1-mixture of a saturated aqueous sodium hydrogen carbonate solution and ether at 0°; the ether phase is washed with 5 ml of a saturated aqueous sodium hydrogen carbonate solution and 5 ml of water, then treated with 3 ml of a concentrated phosphate buffer solution (pH 6) and adjusted to pH 5–6 with 2N aqueous sulphuric acid, and then extracted three times with 15 ml of ether each time. The combined ether solutions are washed with 5 ml of water, dried over sodium sulphate and evaporated. After recrystallisation from a mixture of ether, methylene chloride and hexane, the isomer B of α-(3,3-dimethyl-7-oxo-4-thia-2,6-diaza-6-bicyclo[3,2,0]heptyl)-α-(carboxymethyl)-acetic acid tert.-butyl ester is obtained, m.p. 137°–138°; $[\alpha]_D^{20} = -107° \pm 1°$ (c = 0.7 in chloroform); infra-red absorption spectrum (in methylene chloride): characteristic bands at 5.70μ, 5.78μ, 7.30μ and 8.70μ.

EXAMPLE 40

A mixture of 0.025 g of the isomer B of α-(3,3-dimethyl-7-oxo-4-thia-2,6-diaza-6-bicyclo[3,2,0]heptyl)-α-(carboxymethyl)-acetic acid tert.-butyl ester (Example 39) and 1 ml of trifluoroacetic acid is kept for 18 hours at 0°, is then evaporated under reduced pressure, and the residue containing the α-(3,3-dimethyl-7-oxo-4-thia-2,6-diaza-6-bicyclo[3,2,0]heptyl)-α-(carboxymethyl)-acetic acid, is taken up in 1 ml of dioxane and then mixed with an ether solution of diazomethane until saturated. After 3 minutes reaction time, the mixture is evaporated under reduced pressure and the residue is filtered through a silica gel column (diameter: 0.8 cm; hight: 10 cm), a 2:1-mixture of hexane and ethyl acetate being used for elution; the isomer B of α-(3,3-dimethyl-7-oxo-4-thia-2,6-diaza-6-bicyclo[3,2,0]heptyl)-α-(carbomethoxymethyl)-acetic acid methyl ester of the formula

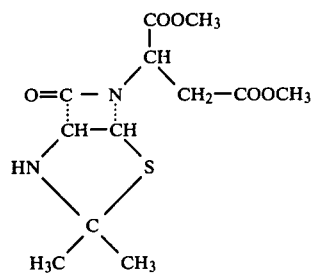

which is obtained as a crude product, melts at 136°–137° after recrystallisation from a mixture of ether, methylene chloride and hexane.

EXAMPLE 41

A solution of 0.1056 g of the isomer A of α-(2-carbo-tert.-butyloxy-3,3-dimethyl-7-oxo-4-thia-2,6-diaza-6-bicyclo[3,2,0]heptyl)-α-(carbo-tert.-butyloxymethyl)-acetic acid 2,2,2-trichloroethyl ester in 1.6 ml of a 84:16-mixture (parts by weight) of trifluoroacetic acid and trifluoroacetic acid anhydride is treated with 12 ml of acetic acid anhydride after standing for 2 hours at room temperature and, after standing for one hour at room temperature, is evaporated under a high vacuum without warming. The residue is dissolved four times in a mixture of methylene chloride and benzene and in each case evaporated to dryness. The residue crystallised from chloroform and yields the 7α-trifluoroacetylamino-4,8-dioxo-5-thia-1-azabicyclo[4,2,-0]octane-2β-carboxylic acid 2,2,2-trichloroethyl ester of the formula

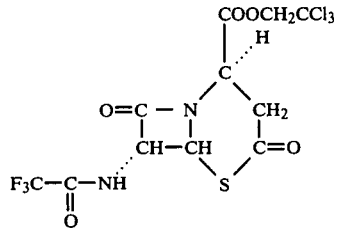

m.p. 175°–176°; infra-red absorption spectrum (in methylene chloride): characteristic bands at 3.07μ, 5.60μ, 5.69μ, 5.79μ, 5.94μ and 6.56μ.

EXAMPLE 42

A solution of 0.017 g of 7α-trifluoroacetylamino-4,8-dioxo-5-thia-1-azabicyclo[4,2,0]octane-2β-carboxylic acid 2,2,2-trichloroethyl ester in 1 ml of 90% aqueous acetic acid is treated over the course of 5 minutes with 0.17 g of activated zinc dust. After 50 minutes, 10 ml of ethyl acetate are added, the mixture is filtered and the filer residue is washed with 10 ml of ethyl acetate. The organic filtrate is washed with 4 ml of a saturated aqueous sodium chloride solution, dried and evaporated under reduced pressure. The resulting oily 7α-trifluoroacetylamino-4,8-dioxo-1-aza-5-thia-bicyclo[4,2,0]octane-2β-carboxylic acid of the formula

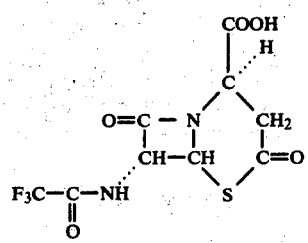

shows in the infra-red absorption spectrum (in potassium bromide) characteristic bands at 5.64μ, 5.83μ, 5.95μ, 6.47μ, 7.12μ, 8.12μ, 8.60μ, 9.60μ and 10.00μ.

EXAMPLE 43

A solution of 0.05 g of the isomer B of α-(2-carbo-tert.-butyloxy-3,3-dimethyl-7-oxo-4-thia-2,6-diaza-6-bicyclo[3,2,0]heptyl)-α-(carbo-tert.-butyloxy-methyl)-acetic acid 2,2,2-trichloroethyl ester in 0.8 ml of a 84:16-mixture (parts by weight) of trifluoroacetic acid and trifluoroacetic acid anhydride is allowed to stand for 2 hours and then treated with 2 ml of acetic acid anhydride. After one hour at room temperature, the volatile components are evaporated under high vacuum without heating and the residue is dissolved in methylenechloride and benzene. The solution is taken to dryness and the operation is repeated three times. The residue crystallised from chloroform to yield the 7α-N-trifluoroacetylamino-4,8-dioxo-5-thia-1-azabicyclo[4,2,0]octan-2β-carboxylic acid 2,2,2-trichloroethyl ester of the formula

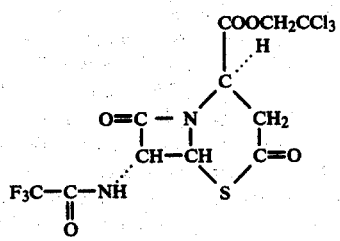

The mother liquors are chromatographed in acid-washed silica gel; a further amount of the desired product is eluted with a 9:1-mixture of benzene and ethyl acetate, which melts at 183°–187° after crystallisation from chloroform; infra-red absorption spectrum (in methylene chloride): characteristic bands at 3.08μ, 5.61μ, 5.71μ, 5.79μ, 5.94μ and 6.56μ.

EXAMPLE 44

A solution of 0.1211 g of isomer A of α-(2-carbo-tert.-butyloxy-3,3-dimethyl-7-oxo-4-thia-2,6-diaza-6-bicyclo[3,2,0]heptyl)-α-(phenylacetylmethylene)-acetic acid tert.-butyl ester in 1.2 ml of pre-cooled trifluoroacetic acid is allowed to stand for 21 hours at −20°, and is then diluted with 9 ml of dioxane. The mixture, containing the 7-amino-4-benzylidene-8-oxo-5-thia-1-azabicyclo[4,2,0]oct-2-ene-2-carboxylic acid (configuration of 7-amino-cephalosporanic acid), is mixed with a solution of 0.129 g of phenyloxyacetyl chloride in 1 ml of dioxane. After standing for 2½ hours at room temperature, the reaction mixture is treated with 1 ml of water and allowed to stand for one additional hour. The volatile portions are removed by lyophilisation under a high vacuum and the residue is chromatographed on 9 g of acid-washed silica gel. Phenyloxyacetic acid and a small quantity of neutral material are eluted with a 100:5-mixture of benzene and acetone and the 4-benzylidene-7-N-phenyloxyacetylamino-8-oxo-5-thia-1-azabicyclo[4,2,0]oct-2-ene-2-carboxylic acid (configuration of 7-amino-cephalosporanic acid) of formula

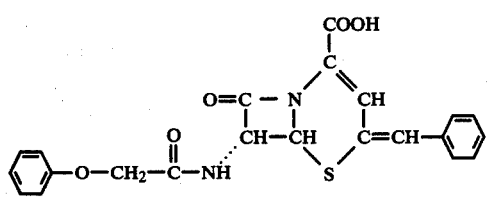

is eluted with a 2:1-mixture of benzene and acetone; the product, in the form of yellowish crystals after recrystallisation from a mixture of acetone and benzene, melts at 191°–193° (decomposition); thin layer chromatogram: Rf = 0.36 (silica gel; system toluene:acetic acid:-water 5:4:1); ultraviolet absorption spectrum: $\lambda_{max}$ 349 mμ and $\lambda_{shoulder}$ 250–265 mμ (in ethanol); $\lambda_{max}$ 345 mμ and $\lambda_{shoulder}$ 250–265 mμ (in potassium hydroxide/ethanol); and $\lambda_{max}$ 357 mμ and $\lambda_{shoulder}$ 250–265 mμ (hydrogen chloride/ethanol); infra-red absorption spectrum (in potassium bromide): characteristic bands at 2.90μ (shoulder) 3.20–4.15μ, 5.62μ, 5.70μ (shoulder), 5.82–5.95μ, 6.00μ (shoulder), 6.10–6.15μ and 6.23–6.33μ (inflection).

EXAMPLE 45

A solution of 0.5625 g of the isomer A of α-(2-carbo-tert.-butyloxy-3,3-dimethyl-7-oxo-4-thia-2,6-diaza-6-bicyclo [3,2,0[heptyl)-α-(phenylacetylmethylene)-acetic acid tert.-butyl ester in 4 ml of trifluoroacetic acid pre-cooled is allowed to stand for 20 minutes at −20° and for one hour at room temperature. After diluting with 30 ml of dry dioxane, the mixture, containing the 7-amino-4-benzylidene-8-oxo-5-thia-1-azabicyclo[4,2,0]-oct-2-ene-2-carboxylic acid (configuration of 7-amino-cephalosporanic acid) is mixed with a solution of 0.5 g of freshly distilled phenylacetic acid chloride in 5 ml of dioxane. The reaction mixture is allowed to stand for 3 hours at room temperature and is then mixed with 2 ml of water; the mixture is allowed to stand for one hour at room temperature, is then cooled to −10°, and the volatile portions are evaporated by lyophilisation under a high vacuum. The residue is taken up in 4 ml of benzene, whereupon crystallisation sets in. After 24 hours the crystalline material is filtered off and is washed with benzene; the 4-benzyliden-7-N-phenylacetyl-amino-8 -oxo-5-thia-1-azabicyclo[4,2,0]-oct-2-ene-2-carboxylic acid (configuration of 7-amino-cephalosporanic acid) of the formula

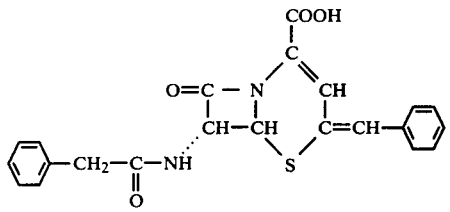

is thus obtained m.p. 224°–226° after recrystallisation from 90% aqueous ethanol; thin layer chromatogram: Rf = 0.30 (silica gel; system toluene:acetic acid:water 5:4:1); ultra-violet absorption spectrum:$\lambda_{max}$ 353 mµ and 250–265 mµ (shoulder) (in ethanol); $\lambda_{max}$ 347 mµ, 250–265 mµ and 240 mµ (shoulder) (in potassium hydroxide/ethanol); and $\lambda_{max}$ 358 mµ and 250–265 mµ (in hydrogen chloride/ ethanol); infra-red absorption spectrum (in potassium bromide): characteristic bands at 3.00µ (shoulder), 3.10–4.10µ, 5.65µ, 5.75µ (shoulder), 5.80µ (shoulder), 5.90–5.95µ, 6.00µ (shoulder), 6.15µ, 6.24µ (shoulder), 6.28¾ (shoulder); 6.55µ, 6.65µ and 6.73µ (shoulder).

The mother liquor is chromatographed on 10 g of acid-washed silica gel; phenylacetic acid together with a yellow neutral material is eluted with a 100:5-mixture of benzene and acetone, and a further quantity of 4-benzylidene-7-N-phenylacetyl-amino-8-oxo-5-thia-1-azabicyclo[4,2,0]-oct-2-ene-2-carboxylic acid is then eluted with a 2:1 mixture of benzene and acetone; this material crystallises after adding a little acetone, melting point 223°–225°.

EXAMPLE 46

A solution of 0.0917 g of the isomer A of α-(2-carbo-tert.-butyloxy-3,3-dimethyl-7-oxo-4-thia-2,6-diaza-6-bicyclo[3,2,0]heptyl)-α-(phenylacetylmethylene)-acetic acid tert.butyl ester in 1 ml of pre-cooled trifluoroacetic acid is allowed to stand for 21 hours at −20° and is then diluted with 7 ml of dioxane. The resulting mixture, containing the 7-amino-4-benzylidene-8-oxo-5-thia-1-azabicyclo[4,2,0]-oct-2-ene-2-carboxylic acid (configuration of 7-amino-cephalosporanic acid), is treated with 10 drops of acetyl chloride. The reaction mixture is allowed to stand at room temperature for 3 hours, the excess acetyl chloride is removed under reduced pressure (oil pump) and 0.8 ml of water is added. After a further hour at room temperature, the volatile portions are evaporated under reduced pressure (oil pump) and the residue is dissolved in 0.7 ml of benzene. The 7-N-acetyl-amino-4-benzylidene-8-oxo-5-thia-1-azabicyclo[4,2,0]-oct-2-ene-2-carboxylic acid (configuration pf 7-amino-cephalosporanic acid) of the formula

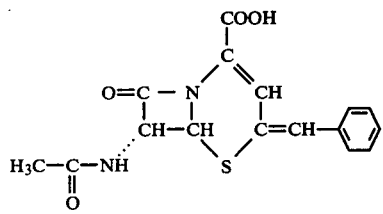

crystallise m.p. 160°–164°; thin layer chromatogram; Rf = 0.16 (silica gel; system toluene:acetic acid:water 5:4:1); ultra-violet absorption spectrum:$\lambda_{max}$ 354 mµ and 250–265 mµ (shoulder) (in ethanol):$\lambda_{max}$ 346 mµ, 250–265 mµ and 240 mµ (shoulder) (in ethanol/potassium hydroxide); and $\lambda_{max}$ 357 mµ and 250–265 mµ (shoulder) (in ehtanol/hydrogen chloride); infra-red absorption spectrum (in potassium bromide); characteristic bands at 2.90µ (shoulder), 3.15–4.20µ, 5.63–5.71µ, 5.75µ (shoulder), 5.80–5.94µ (inflection); 6.00µ (shoulder), 6.04–6.13µ and 6.40–6.70µ (inflection).

The mother liquor is chromatographed on 5 g of acid-washed silica gel; a further quantity of the desired 7-N-acetyl-amino-4-benzylidene-8-oxo-5-thia-1-azabicyclo[4,2,0]-oct-2-ene-2-carboxylic acid together with a neutral product, which is enriched in the first fractions, are eluted with a 4:1-mixture of benzene and acetone.

EXAMPLE 47

A suspension of 0.0198 g of 4-benzylidene-7-N-phenylacetyl-amino-8-oxo-5-thia-1-azabicyclo[4,2,0]-oct-2-ene-2-carboxylic acid in 1.5 ml of methanol, cooled in ice water, is treated in portions with an excess of a 2% solution of diazomethane is ether; the evolution of nitrogen sets in immediately and the solid material dissolves. The addition of diazomethane is stopped as soon as the yellow discolouration persists for 2–3 minutes. The volatile portions are removed in a rotational evaporator and the residue is crystallised by adding a few drops of methanol. The resulting 4-benzylidene-7-N-phenylacetylamino-8-oxo- 5-thia-1-azabicyclo[4,2,-0]oct-2-ene-2-carboxylic acid methyl ester (configuration of 7-amino-cephalosporanic acid) of formula

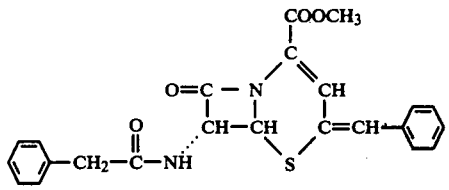

melts at 193°–195.5°; $[\alpha]_D^{20}$ = −325 ± 1° (c = 1 in chloroform); thin layer chromatogram: Rf = 0.22 (silica gel; system hexane; ethyl acetate 2:1); ultra-violet absorption spectrum:$\lambda_{max}$ 360 mµ ($\epsilon$ = 24,800) and 262 mµ ($\epsilon$ = 8,100) (in ethanol): $\lambda_{max}$ 362 mµ and 250 mµ (shoulder) (in potassium hydroxide/ethanol); and $\lambda_{max}$ 362 mµ and 250–265 mµ (shoulder) (in hydrogen chloride/ethanol); infra-red absorption spectrum (in methylene chloride): characteristic bands at 3.06µ, 5.62µ, 5.82µ, 5.95µ, 6.00µ (shoulder), 6.24µ, 6.30µ (shoulder), 6.62µ(shoulder) and 6.65–6.73µ.

EXAMPLE 48

A mixture of 0.1158 g of α-(2-carbo-tert.-butyloxy-3,3-dimethyl-7-oxo-4-thia-2,6-diaza-6-bicyclo[3,2,0]-heptyl)-α-(isobutyrylmethylene)-acetic acid tert.-butyl ester (isomer A) in 1 ml of pre-cooled trifluoroacetic acid is allowed to stand for 22 hours at −20° . 5 ml of dry dioxane are added and the mixture, containing the 7-amino-4-isopropylidene-8-oxo-5-thia-1-azabicyclo[4,2,0]oct-2-ene-2-carboxylic acid (confirguration of 7-amino-cephalosporanic acid) is treated with 0.123 g of phenylacetyl chloride. After standing for 3 hours at room temperature, 10 drops of water are added and after a further hour the volatile portions are distilled off under a high vacuum. The oily residue is chromatographed on 10 g of acid-washed silica gel. Phenylacetic acid and a small quantity of a neutral product are eluted with a 100:5-mixture of benzene and acetone. The 4-isopropylidene-7-N-phenylacetyl-amino-8-oxo-5-thia-1-azabicyclo[4,2,0]oct-2-ene-carboxylic acid (configuration of 7-amino-cephalosporanic acid) of the formula

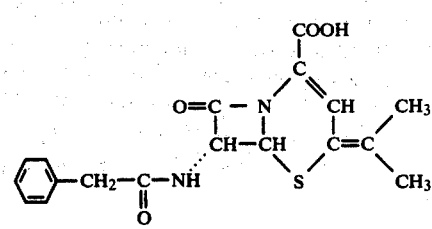

is eluted with a 2:1-mixture of benzene and acetone. It melts at 216°–219° after crystallisation from benzene, containing a small quantity of acetone; infra-red absorption spectrum:$\lambda_{max}$ 326 m$\mu$ (in ethanol);$\lambda_{max}$ 317 m$\mu$ (in potassium hydroxide/ethanol); and $\lambda_{max}$ 332 m$\mu$ (in hydrogen chloride/ethanol; infra-red absorption spectrum (in potassium bromide); characteristic bands at 3.00$\mu$ (shoulder), 3.15–4.35$\mu$, 5.60$\mu$, 5.65$\mu$(shoulder), 5.90$\mu$, 6.04$\mu$, 6.25$\mu$, 6.30$\mu$(shoulder) and 6.45–6.55$\mu$.

EXAMPLE 49

A mixture of 0.128 g of the isomer A of α-(2-carbo-tert.-butyloxy-3,3-dimethyl-7-oxo-4-thia-2,6-diaza-6-bicyclo[3,2,0]heptyl)-α-[(4-nitrophenylacetyl)-methylene]-acetic acid tert.-butyl ester in 1 ml of trifluoroacetic acid is allowed to stand for 44 hours at −20°. The orange-coloured reaction mixture, containing the 7-amino-4-(4-nitrobenzylidene)-8-oxo-5-thia-1-azabicyclo[4,2,0]-oct-2-ene-2-carboxylic acid (configuration of 7-amino-cephalosporanic acid), is diluted with 5 ml of dry dioxane and mixed with a solution of 0.155 g of phenylacetyl chloride in 2 ml of dioxane. After standing for 3 hours at room temperature, 0.5 ml of water is added and after a further 60 minutes at room temperature, the volatile portions are removed under an oil pump vacuum. The residue is mixed with a few drops of methylene chloride and benzene; an orange-yellow precipitate forms, which is filtered off and washed on the filter with a few drops of methylene chloride. The 4-(4-nitrobenzylide)-7-N-phenylacetyl-amino-8-oxo-5-thia-1-aza-bicyclo[4,2,0]oct-2-ene-2-carboxylic acid (configuration of 7-amino-cephalosporanic acid) of the formula

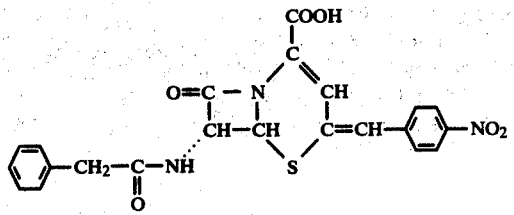

is thus obtained, After recrystallisation from a mixture of acetone and benzene, this material melts at 202°–204°; ultraviolet absorption spectrum; $\lambda_{max}$ 390 m$\mu$ and 273 m$\mu$orange-coloured (weak) (in ethanol), $\lambda_{max}$ 398 m$\mu$ and about 275 m$\mu$ (weak) (in potassium hydroxide/ethanol); and $\lambda_{max}$ 392 m$\mu$ and about 275 m$\mu$ (weak) (in hydrogen chloride/ethanol); infra-red absorption spectrum (in potassium bromide); characteristic bands at 2.9–4.2$\mu$ (broad), 5.60–5.65$\mu$, 5.80–6.0$\mu$; 6.05$\mu$, 6.25$\mu$, 6.60$\mu$ and 7.45$\mu$.

EXAMPLE 50

A solution of 0.023 g of crude 4-(4-nitrobenzylidene)-7-N-phenylacetyl-amino-8-oxo-5-thia-1-azabicyclo[4,2,-0]oct-2-ene-2-carboxylic acid (configuration of 7-amino-cephaloasporanic acid), obtained from the crystallisation mother liquor, in 1 ml of methanol is treated with an excess of diazomethane in ether and allowed to stand at room temperature for a few minutes, and is then evaporated in a rotational evaporator.

The residue is purified by means of thin layer chromatography (silica gel plate: 20 × 20 × 0.15 cm), using a 2:1-mixture of hexane and ethyl acetate and ethyl acetate alone. The orange-colored band is extracted with ethyl acetate and the 4-(4-nitrobenzylidene)-7-N-phenylacetyl-amino-8-oxo-5-thia-1-azabicyclo[4,2,-0]oct-2-ene-2-carboxylic acid methyl ester (configuration of 7-amino-cephalosporanic acid) of the formula

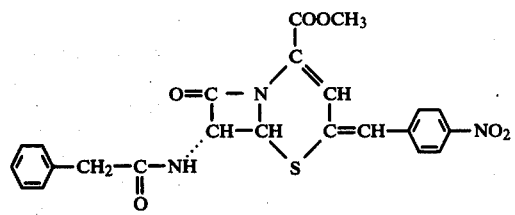

is thus obtained; it crystallises after prolonged standing m.p. 185°–187° (with decomposition); ultra-violet absorption spectrum:$\lambda_{max}$ 382 m$\mu$ and 278 m$\mu$ (shoulder) (in ethanol), $\lambda_{max}$ 380 m$\mu$ and 278 m$\mu$ (shoulder) (in potassium hydroxide/ethanol) and $\lambda_{max}$ 378 m$\mu$ and 278 m$\mu$ (shoulder) (in hydrogen chloride/ethanol); infra-red absorption spectrum (in methylene chloride); characteristic bands at 3.03$\mu$, 5.60$\mu$, 5.81$\mu$, 5.95$\mu$, 6.24–6.30$\mu$, 6.60–6.65$\mu$, 6.70$\mu$ (shoulder) and 7.46$\mu$.

EXAMPLE 51

A solution of 0.12 g of isomer A of α-(2-carbo-tert.-butyloxy-3,3-dimethyl-7-oxo-4-thia-2,6-diaza-6-bicyclo[3,2,0]heptyl)-α-[(4-methoxy-phenylacetyl)-methylene]-acetic acid tert.-butyl ester in 1 ml of precooled trifluoroacetic acid is allowed to stand for 2 hours at −20°. The reaction mixture, which contains the 7-amino-4-(4-methoxybenzylidene)-8-oxo-5-thia-1-azabicyclo[4,2,0]oct-2-ene-2-carboxylic acid (configuration of 7-amino-cephalosporanic acid) is mixed with 5 ml of dioxane and treated with a solution of 0.154 g of phenylacetyl chloride in 2 ml of dry dioxane. After 3 hours at room temperature, 10 drops of water are added and the solution is allowed to stand for an additional hour. The volatile portions are then evaporated off under a high vacuum and the oily residue is chromatographed on 10 g of acid-washed silica gel (column). The excess phenylacetic acid is eluted with benzene, containing 5% of acetone, together with a yellow-coloured product. The 4-(4-methoxybenzylidene)-7-N-phenylacetyl-amino-8-oxo-5-thia-1-azabicyclo[4,2,0]oct-2-ene-2-carboxylic acid (configuration of 7-amino-cephalosporanic acid) of the formula

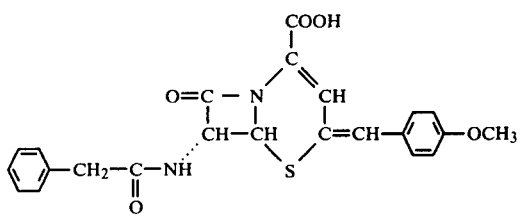

is eluted with a 2:1-mixture of benzene and acetone and melts, after crystallisation from a mixture of acetone and benzene, as a yellow product at 201°–203°; ultra-violet absorption spectrum:$\lambda_{max}$ 366μ and 275 mμ (shoulder) (in ethanol); $\lambda_{max}$ 356 mμ and 272 mμ (shoulder) (in potassium hydroxide/ethanol) and $\lambda_{max}$ 372 mμ and 277 mμ (shoulder) (in hydrogen chloride/ethanol); infra-red absorption spectrum (in potassium bromide): characteristic bands at 2.95μ (shoulder), 3.01–4.40μ, 5.64–5.70μ, 5.75μ (inflection), 6.04–6.10μ, 6.28μ and 6.61μ.

EXAMPLE 52

A mixture of 0.0052 g of 4-(4-methoxybenzylidene)-7-N-phenylacetyl-amino-8-oxo-5-thia-1-azabicyclo[4,2,0]oct-2-ene-2-carboxylic acid (configuration of 7-amino-cephalosporanic acid) in 2 ml of methanol is mixed with 2 ml of a 2% solution of diazomethane in ether. The mixture is allowed to stand for 3 minutes at room temperature, the volatile portions are then evaporated off and the residue is crystallised from a mixture of methanol and ether. The resulting 4-(4-methoxybenzylidene)-7-N-phenylacetyl-amino-8-oxo-5-thia-1-azabicyclo[4,2,0]-oct-2-ene-2-carboxylic acid methyl ester (configuration of 7-amino- cephalosporanic acid) of the formula

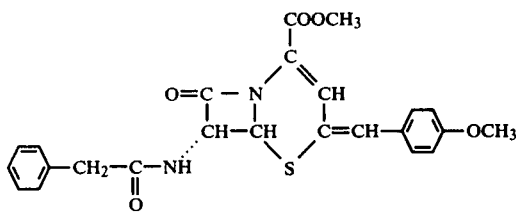

melts at 210°–211°; ultra-violet absorption spectrum: $\lambda_{max}$ 378 mμ and 278 mμ (shoulder) (in ethanol); $\lambda_{max}$ 376 mμ and 278 mμ (shoulder) (in potassium hydroxide/ethanol) and $\lambda_{max}$ 374 mμ (in hydrogen chloride/ethanol); infra-red absorption spectrum (in methylene chloride): characteristic bands at 3.02μ, 5.60μ, 5.80μ, 5.9μ, 6.26μ, 6.60–6.65μ and 7.12μ.

EXAMPLE 53

A solution of 0.232 g of the isomer A of 60 -(2carbo-tert.-butyloxy-3,3-dimethyl 7-oxo-4-thia-2,6-diaza-6-bicyclo [3,2,0]heptyl)-60-[(4-chlorophenylacetyl)-methylene]-acetic acid tert.-butyl ester in 2 ml of trifluoroacetic acid is allowed to stand for 21 hours at −20°. After 20 minutes at room temperature, the mixture, which contains the 7-amino-4-(4-chlorobenzylidene)-8-oxo-5-thia-1-azabicyclo[4,2,0]oct-2-ene-2-carboxylic acid (configuration of 7-amino-cephalosporanic acid) is treated with 15 ml of dry dioxane, followed by 0.25 g of freshly distilled phenylacetyl chloride. The solution is kept for 3 hours at room temperature, then treated with 0.3 ml of water and allowed to stand for one hour at room temperature. The volatile components are removed under reduced pressure (oil pump, room temperature), and the residue is chromatographed on 10 g of acid-washed silica gel. Phenylacetic acid and a small amount of a neutral by-product are eluted with 250 ml of a 100:5-mixture of benzene and acetone. With a 2:1-mixture of benzene and acetone the 4-(4-chlorobenzylidene)-7-N-phenylacetyl-amino-8-oxo-5-thia-1-azabicyclo[4,2,0]oct-2-ene-2-carboxylic acid (configuration of 7-amino-cephalosporanic acid) of the formula

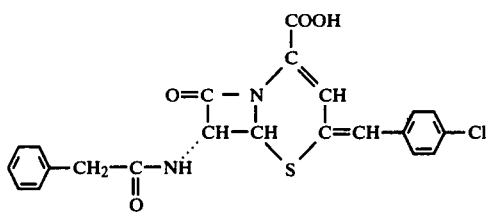

is eluted which crystallises in the form of yellowish crystals on the addition of a small amount of benzene and ethyl acetate, m.p. 226°–227°; ultra-violet absorption spectrum:$\lambda_{max}$ 359 mμ (in ethanol); $\lambda_{max}$ 351 mμ (in potassium hydroxide/ethanol) and infra-red $_{max}$ 362 mμ (in hydrogen chloride/ethanol); infrared absorption spectrum (in potassium bromide): characteristic bands at 2.85–4.30μ (broad), 3.02μ, 5.62μ, 5.88μ, 6.15β, 6.26μ, 6.55 and 6.70μ.

EXAMPLE 54

A solution of 0.3285 g of the isomer A (trans) of α-(2-carbo-tert.-butyloxy-3,3-dimethyl-7-oxo-4-thia-2,6-diaza 6-bicyclo[3,2,0]heptyl)-α-(cyclohexylacetyl-methylene)-acetic acid tert.-butyl ester in 2.3 ml of precooled tri-fluoroacetic acid is allowed to stand for 16-½ hours at −20°. The reaction mixture, containing the 7-amino-4-cyclo-hexylmethylene-8-oxo-5-thia-1-azabicyclo[4,2,0]oct-2-en-2-carboxylic acid (configuration of 7-amino-cephalosporanic acid), is trated with 0.13 g of phenylacetyl chloride in 14 ml of dioxane and allowed to stand for 3 hours at room temperature. After an additional hour, 0.3 ml of water is added, the volatile components are removed under reduced pressure (oil pump, room temperature), and the residue is chromatograhed on 10 g of acid-washed silica gel. Phenylacetic acid and a small amount of neutral substances are removed with a 100:5-mixture of benzene and acetone, and with a 2:1-mixture of benzene and acetone; there is eluted the 4-cyclohexylmethylene-7-N-phenylacetyl-amino-8-oxo-5-thia-1-azabicyclo[4,2,0]oct-2-ene-2-carboxylic acid (configuration of 7-amino-cephalosporanic acid) of the formula

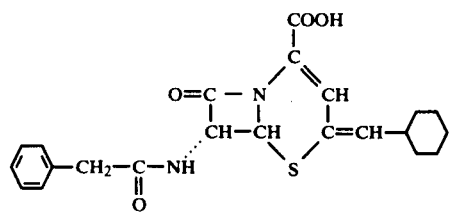

which after crystallisation from benzene melts at 120°–121°; ultra-violet absorption spectrum:$\lambda_{max}$ 317 mμ (in ethanol), $\lambda_{max}$ 309 mμ (in potassium hydroxide/ethanol) and $\lambda_{max}$ 323 mμ (in hydrogen chloride/ethanol); infra-red absorption spectrum (in methylene chloride): characteristic bands at 2.96μ, 3.45μ, 3.53μ, 2.85–4.3μ (broad), 5.61μ, 5.70–5.85μ (broad), 5.94μ, 6.05μ (shoulder), 6.24μ and 6.60–6.70μ.

EXAMPLE 55

A mixture of 0.4 g of α-(2-carbo-tert.-butyloxy-3,3-dimethyl-7-oxo-4-thia-2,6-diaza-6-bicylco[3,2,0]heptyl)-α-(phenylacetylmethyene)-acetic acid tert.-butyl ester in 4 ml of trifluoroacetic acid is allowed to stand for 20 hours at −20°. The trifluoroacetic acid is removed under reduced pressure (oil pump) and the orange-coloured residue, containing the 7-amino-4-benzylidene-8-oxo-5-thia-1-azabicyclo[4,2,0]oct-2-en-2-carboxylic acid (configuration of 7-amino-cephalosporanic acid), is treated with 4 ml of a solution, cooled to −15°, of the mixed anhydride of cyanoacetic acid and trichloroacetic acid in methylene chloride. (The mixed anhydride may be obtained as follows: A mixture of 1.45 of cyanoacetic acid in 3 ml of methylene chloride is treated with 1.1 ml of triethylamine and the resulting solution, cooled to 31 5°, is added with stirring to a solution, maintained at −15°, of 1.45 g of trichloroacetyl chloride in 3 ml of methylene chloride. A suspension is thus obtained which is made up to a volume of 14ml with methylene chloride at 15° and used in this form). The reaction mixture is treated with 2 ml of a solution of 0.3 ml of acetic acid and 1 ml of triethylamine in 6 ml of methylene chloride, stirred for 2 hours at room temperature and then diluted with 30 ml of ethyl acetate. The reaction mixture is washed with a concentrated aqueous sodium chloride solution containing hydrochloric acid (15 ml of the sodium chloride solution contains 1.5 ml of 1N hydrochloric acid), and with a concentrated aqueous sodium chloride solution, dried over sodium sulphate and evaporated under reduced pressure. The residue is treated with about 1 ml of ethyl acetate and diluted cautiously with ether and then allowed to stand, to yield the crystalline 4-benzylidene-7-N-cyanoacetylamino-8-oxo-5-thia-1-azabicyclo[4,2,0]oct-2-en-2-carboxylic acid (configuration of 7-amino-cephalosporanic acid) of the formula

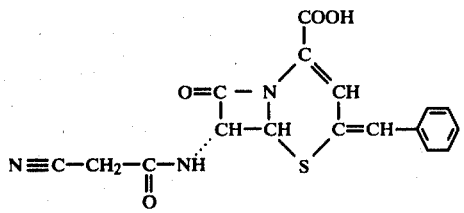

The residue from the mother liquor is chromatographed on 20 g of acid-washed silica gel, eluting with a 100:5-mixture of benzene and acetone neutral components, cyanoacetic acid and trichloroacetic acid, and with a 2:1-mixture of benzene and acetone a further quantity of the desired product which, after crystallisation from ethyl acetate and ether, melts at 225°-227° with decomposition; ultra-violet absorption spectrum:-$\lambda_{max}$ 353 mμ and 240–265 mμ (broad shoulder) (in ethanol), $\lambda_{max}$ 346 mμ and 248 mμ (shoulder) (in potassium hydroxide/ethanol) and $\lambda_{max}$ 356 mμ and 247 mμ (shoulder) (in hydrogen chloride/ethanol); infra-red absorption spectrum (in potassium bromide): characteristic bands at 2.90–4.20μ, 4.42μ, 5.60μ, 5.85–5.90μ, 5.98μ, 6.22μ and 6.45μ.

EXAMPLE 56

A solution of 0.023 g of 4-benzylidene-7-N-cyanoacetyl-amino-8-oxo-5-thia-1-azabicyclo[4,2,0]oct-2-en-2carboxylic acid configuration of 7-amino-cephalosporanic acid) in about 2 ml of methanol is treated with a large excess of a 2% solution of diazomethane in ether. After standing for 2 minutes at room temperature the excess of diazomethane and the solvent are evaporated and the crystalline residue is purified by means of preparative thin-layer chromatography on a silica gel plate, a 95:5-mixture of chloroform and methanol being used. The 4-benzylidene-7-N-cyanoacetylamino-8-oxo-5-thia-1-azabicyclo[4,2,0]oct-2-en-2-carboxylic acid methyl ester configuration of 7-amino-cephalosporanic acid) of the formula

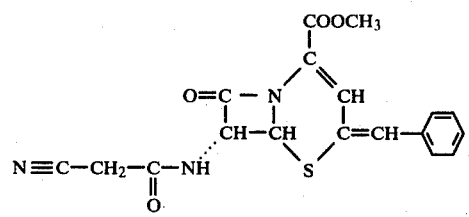

is obtained in crystalline form; m.p. 232°–234°; ultra-violet absorption spectrum:$\lambda_{max}$ 356 mμ and 247–265 mμ (broad shoulder) (in ethanol),$\lambda_{max}$ 364 mμ and 253 mμ (in potassium hydroxide/ethanol) and $\lambda_{max}$ 364 mμ and 254 mμ (on acidifying the alkaline sample with hydrogen chloride/ethanol; infra-red absorption spectrum (in mineral oil): characteristic bands at 3.1μ, 5.60–5.64μ, 5.80μ, 5.98μ, 6.20μ, 6.45μ and 6.50μ (shoulder).

EXAMPLE 57

A mixture of 0.328 g of α- (2-carbo-tert.-butyloxy-3,3-dimethyl-7-oxo-4-thia-2,6-diaza-6-bicyclo[3,2,0]heptyl)-α-(4-nitrophenylacetyl-methylene)-acetic acid tert.-butyl ester and 3 ml of trifluoroacetic acid is allowed to stand for 44 hours at −20°. The trifluoroacetic acid is removed under reduced pressure (oil pump) and the residue, containing the 7-amino-4-(4-nitrobenzylidene)-8-oxo-5-thia-1-azabicyclo[4,2,0]oct-2-en-2-carboxylic acid (configuration of 7-amino-cephalosporanic acid), is treated with 3 ml of a solution of the mixed anhydride of cyanoacetic acid and trichloroacetic acid in methylene chloride (prepared as described in Example 55), followed by 1.5 ml of a solution of 0.3 ml of acetic acid and 1 ml of triethylamine in 6 ml of methylene chloride. The reaction mixture is maintained at room temperature for 2 hours, then diluted with 15 ml of ethyl acetate and washed with a concentrated aqueous sodium chloride solution containing hydrochloric acid (10 ml of the sodium chloride solution contain 1 ml of 1N hydrochloric acid), and with a concentrated aqueous sodium chloride solution, dried over sodium sulphate and evaporated under reduced pressure. The residue is chromatographed on 10 g of acid-washed slica gel. With a 100:5-mixture of benzene and acetone an excess of the cyanoacetic acid and trichloroacetic acid and an orange-coloured neutral component are eluted, and with a 2:1-mixture of benzene and acetone the amorphous yellow-orange 7-N-cyanoacetylamino-4-(4-nitro-benzylidene)-5-thia-1-azabicylco[4,2,0]oct-2-en-2-carboxylic acid (configuration of 7-amino-cephalosporanic acid) of the formula

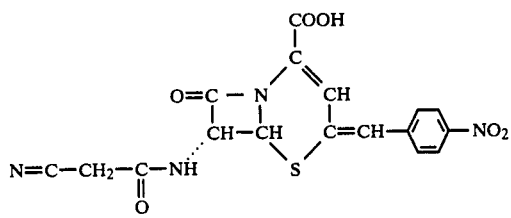

is obtained, ultra-violet absorption spectrum:$\lambda_{max}$ 388 mµ and 275 mµ (in ethanol), $\lambda_{max}$ 453 mµ and 263 mµ (in potassium hydroxide/ethanol) and $\lambda_{max}$ 420 mµ and 263 mµ (after acidifying the alkaline sample with hydrogen chloride/ethanol); infra-red absorption spectrum (in potassium bromide): characteristic bands at 2.8–4.2µ, 5.60–5.65µ, 5.80–6.07µ, 6.25µ, 6.60µ and 7.45µ.

Pharmacologically active compounds of the above type are preferably used in the form of pharmaceutical preparations in which they are present mixed with a solid or liquid pharmaceutical excipient, and which are suitable for enteral or parenteral administration. Suitable excipients which are inert towards the active substances are, for example, water gelatine, saccharides, such as lactose, glucose or sucrose, starches, such as corn starch, wheat starch or arrowroot, stearic acid or salts thereof, such as magnesium or calcium stearate, talc, vegetable fats and oils, alginic acid, benzyl alcohols, glycols or other known excipients. The preparations can be in a solid form, for example, as tablets, dragees, capsules or suppositories, or in a liquid form, for example, as solutions, suspensions or emulsions. They may be sterilised and/or contain auxiliary substances such as peservatives, stabilizers, wetting agents or emulsifiers, solubilizers, salts for regulating the osotic pressue and/or buffers. They can, furthermore, contain other pharmacologically useful substances. The pharmaceutical preparations can be formulated in a manner which is is itself known.

We claim:

1. A compound of the formula Ia

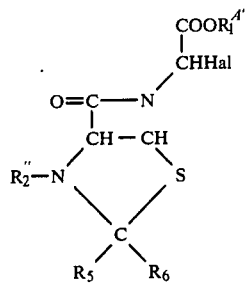

in which
 R$^{A'}_1$ represents a member selected from the group consisting of lower alkyl of 1–4 carbon atoms, halogenolower alkyl of 1–4 carbon atoms, adamantyl, monocyclic cycloalkyl with 3 to 8 ring carbon atoms and phenyl-lower alkyl,
 R''$_2$ is carbo lower alkoxy with up to 7 carbon atoms in the lower alkyl residue, carbovinyloxy, carbocycloalkoxy, wherein cycloalkyl is monocyclic cycloalkyl with 3 to 6 ring carbon atoms or adamantyl, carbobenzyloxy, carbodiphenylmethoxy or carbo(α-4-biphenylyl-α-methyl-ethoxy), each of the substituents R$_5$ and R$_6$ represents a lower alkyl of from 1–4 carbon atoms and Hal represents a member selected from the group consisting of a chlorine and bromine atom.

2. A compound as claimed in claim 1 and being an α-(2-carbo-lower alkoxy-3,3-dimethyl-7-oxo-4-thia-2,6-diaza-6-bicyclo-[3,2,0]heptyl)-α-Hal-acetic acid lower alkyl ester, in which Hal represents a member selected from the group consisting of a chlorine and bromine atom, and the lower alkyl group of the lower alkyl ester is a member selected from the group consisting of lower alkyl 2,2,2-trichloroethyl and 2-iodo-ethyl.

3. A compound as claimed in claim 1 and being the α(2-Carbo-tert.-butyloxy-3,3-dimethyl-7-oxo-4-thia-2,6-diaza-6-bicyclo[3,2,0]heptyl)-α-chloro-acetic acid 2,2,2-trichloroethyl ester.

4. A compound as claimed in claim 1 and being the α-(2-Carbo-tert.-butyloxy-3,3-dimethyl-7-oxo-4-thia-2,6-diaza-6-bicyclo[3,2,0]heptyl)-α-chloro-acetic acid tert.-butyl ester.

5. A compound as claimed in claim 1 and being the α-(2-Carbo-tert.-butyloxy-3,3-dimethyl-7-oxo-4-thia-2,6-diaza-6-bicyclo[3,2,0]-heptyl)-α-bromo-acetic acid 2,2,2-trichloroethyl ester.

* * * * *